United States Patent
Nakai

(10) Patent No.: US 10,241,043 B2
(45) Date of Patent: Mar. 26, 2019

(54) MICRO OBJECT DETECTION APPARATUS

(71) Applicant: MITSUBISHI ELECTRIC CORPORATION, Tokyo (JP)

(72) Inventor: Kenya Nakai, Tokyo (JP)

(73) Assignee: MITSUBISHI ELECTRIC CORPORATION, Tokyo (JP)

(*) Notice: Subject to any disclaimer, the term of this patent is extended or adjusted under 35 U.S.C. 154(b) by 0 days.

(21) Appl. No.: 15/772,405

(22) PCT Filed: Dec. 8, 2016

(86) PCT No.: PCT/JP2016/086550
§ 371 (c)(1),
(2) Date: Apr. 30, 2018

(87) PCT Pub. No.: WO2017/104533
PCT Pub. Date: Jun. 22, 2017

(65) Prior Publication Data
US 2018/0321147 A1    Nov. 8, 2018

(30) Foreign Application Priority Data

Dec. 14, 2015  (JP) .................. 2015-243250
Feb. 2, 2016   (JP) .................. 2016-017780

(51) Int. Cl.
G01N 21/49   (2006.01)
G01N 15/06   (2006.01)
(Continued)

(52) U.S. Cl.
CPC .......... G01N 21/49 (2013.01); G01N 15/0205 (2013.01); G01N 15/0211 (2013.01);
(Continued)

(58) Field of Classification Search
CPC .... G01N 21/49; G01N 15/0211; G01N 15/06; G01N 21/21
See application file for complete search history.

(56) References Cited

U.S. PATENT DOCUMENTS 3,946,239 A * 3/1976 Salzman ............... G01N 21/05
                                                250/461.2
4,188,543 A * 2/1980 Brunsting .......... G02B 19/0028
                                                250/373
(Continued)

FOREIGN PATENT DOCUMENTS

JP    60190835 A    8/1985
JP    61-160048 A   7/1986
(Continued)

OTHER PUBLICATIONS

Extended European Search Report issued in corresponding European Application No. 16875513.0 dated Sep. 14, 2018.
(Continued)

Primary Examiner — Roy M Punnoose
(74) Attorney, Agent, or Firm — Birch, Stewart, Kolasch & Birch, LLP.

(57) ABSTRACT

A micro object detection apparatus includes an optical system. The first optical system includes a first reflection region, a second reflection region, and a light reception element. The first reflection region has an ellipsoidal shape, and reflects scattered light scattered when irradiation light hits a particle to direct the scattered light to the light reception element, by utilizing two focal point positions of the ellipsoidal shape. The second reflection region reflects scattered light coming from the particle to direct the scattered light to the first reflection region, so that the scattered light is directed to the light reception element by utilizing the ellipsoidal shape of the first reflection region. The light flux diameter of the scattered light reflected by the second
(Continued)

reflection region is larger than the particle, at the position of the particle at which the scattered light is generated.

4 Claims, 18 Drawing Sheets

(51) Int. Cl.
- *G01N 21/53* (2006.01)
- *G01N 15/14* (2006.01)
- *G01N 15/02* (2006.01)
- *G01N 21/21* (2006.01)
- G01N 21/03 (2006.01)
- G01N 21/05 (2006.01)
- G01N 15/00 (2006.01)

(52) U.S. Cl.
CPC ......... *G01N 15/06* (2013.01); *G01N 15/1434* (2013.01); *G01N 15/1459* (2013.01); *G01N 21/21* (2013.01); *G01N 21/53* (2013.01); G01N 21/0303 (2013.01); G01N 21/05 (2013.01); G01N 2015/0046 (2013.01); G01N 2015/0053 (2013.01); G01N 2015/0687 (2013.01); G01N 2015/0693 (2013.01); G01N 2015/1452 (2013.01); G01N 2015/1486 (2013.01); G01N 2015/1488 (2013.01); G01N 2015/1493 (2013.01)

(56) References Cited

U.S. PATENT DOCUMENTS

| | | | | | |
|---|---|---|---|---|---|
| 4,273,443 | A * | 6/1981 | Hogg | ................ | G01N 15/1436 250/574 |
| 4,597,665 | A * | 7/1986 | Galbraith | ................ | G01J 1/04 250/559.11 |
| 5,767,967 | A * | 6/1998 | Yufa | ................ | G01N 15/0205 250/458.1 |
| 6,239,710 | B1 * | 5/2001 | Oppelt | ................ | G08B 17/107 340/577 |
| 7,119,899 | B2 * | 10/2006 | Pochy | ................ | G01N 15/0205 356/338 |
| 7,502,110 | B2 * | 3/2009 | Saunders | ........... | G01N 15/1459 356/336 |
| 2004/0066513 | A1 | 4/2004 | Okumura et al. | | |
| 2006/0017926 | A1 | 1/2006 | Pochy et al. | | |
| 2010/0045982 | A1 | 2/2010 | Tsuneta et al. | | |
| 2017/0030822 | A1 * | 2/2017 | Matsunami | ........ | G01N 15/1404 |

FOREIGN PATENT DOCUMENTS

| | | |
|---|---|---|
| JP | 7-504497 A | 5/1995 |
| JP | 9-502254 A | 3/1997 |
| JP | 2004-125602 A | 4/2004 |
| JP | 2006-528348 A | 12/2006 |
| JP | 2007-199012 A | 8/2007 |
| JP | 2011-506977 A | 3/2011 |
| WO | WO 93/17322 A1 | 9/1993 |
| WO | WO 95/09354 A1 | 4/1995 |
| WO | WO 2005/05610 A2 | 2/2005 |
| WO | WO 2007/063862 A1 | 6/2007 |
| WO | WO 2009/076678 A1 | 6/2009 |
| WO | WO 2015/073911 A1 | 5/2015 |

OTHER PUBLICATIONS

Office Action issued in counterpart Japanese Patent Application No. 2017-556010, dated Jan. 22, 2019, with a Machine English Translation.

* cited by examiner

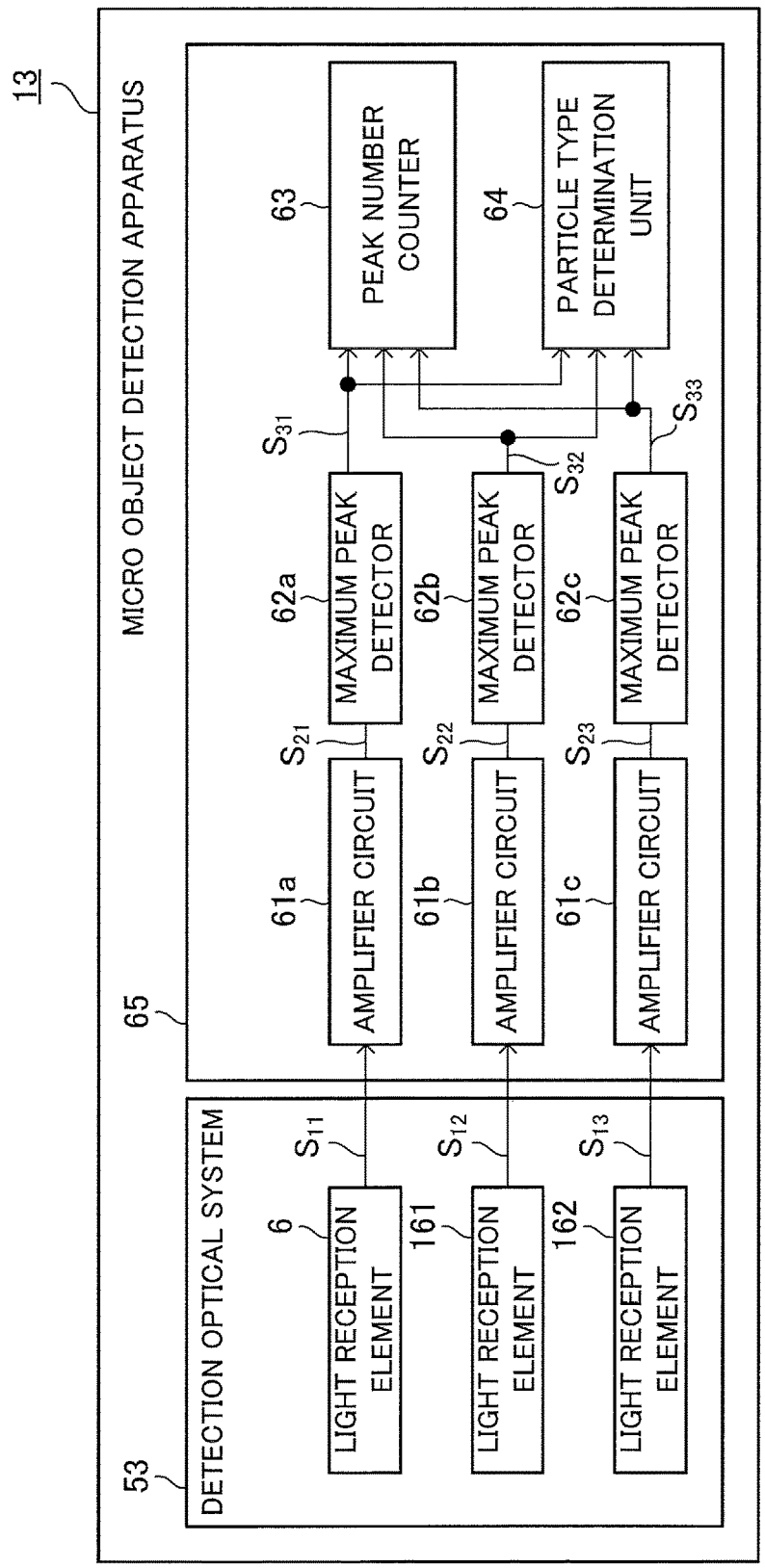

MICRO OBJECT DETECTION APPARATUS

TECHNICAL FIELD

The present invention relates to a micro object detection apparatus that has a function for detecting a particle suspended in the air or a particle suspended in liquid.

BACKGROUND ART

There are various proposals of a micro object detection apparatus that irradiates with light a space in which suspended micro particulate matter (hereinafter referred to as "particle(s)") such as pollen or dust exists, detects scattered light generated at that time, and detects an amount of particles, the size of particles, kinds of particles, or the like.

For example, patent reference 1 discloses a particle sensor that includes a light source, a light reception element, and converging mirrors, to irradiate a particle with light emitted from the light source, reflect scattered light by the converging mirrors, and detect the intensity of the scattered light by the light reception element.

In the particle sensor described in patent reference 1, the two opposite converging mirrors are an elliptical mirror and a spherical mirror. A passage region where a particle that radiates scattered light passes through is located at the position of one focal point (first focal point) of the elliptical mirror. In addition, the light reception element for receiving the scattered light is located at the position of the other focal point (second focal point) of the elliptical mirror. The focal point (the center point of the curvature radius of a spherical mirror surface) of the spherical mirror is positioned at the position of the first focal point of the elliptical mirror. Accordingly, it is possible to further reflect the reflected light from the spherical mirror by the elliptical mirror and to direct the reflected light to the light reception element.

PRIOR ART REFERENCE

Patent Reference

Patent Reference 1: WO2007-063862

SUMMARY OF THE INVENTION

Problem to be Solved by the Invention

However, the light reflected from the spherical mirror is again converged to the particle. Hence, the light reflected from the spherical mirror is blocked by the particle itself, and does not reach the light reception element. This results in decrease in scattered light detection efficiency. In addition, there is a problem that it becomes difficult to detect the particle in a detection circuit for detecting the particle on the basis of an output signal from the light reception element.

Thus, the present invention is made to solve the above problem of the conventional technology. Its purpose is to provide a micro object detection apparatus capable of preventing decrease in efficiency in detecting scattered light and improving accuracy in detecting the particle, by reducing light blocking by a particle itself in a particle sensor that uses two opposite converging mirrors.

Means of Solving the Problem

The micro object detection apparatus according to the present invention includes a first optical system including a first reflection region, a second reflection region, and a light reception element. The first reflection region has an ellipsoidal shape, and reflects scattered light scattered when irradiation light hits a particle, to direct the scattered light to the light reception element, by utilizing two focal point positions of the ellipsoidal shape. The second reflection region reflects scattered light coming from the particle to direct the scattered light to the first reflection region, so that the scattered light is directed to the light reception element by utilizing the ellipsoidal shape of the first reflection region. A light flux diameter of the scattered light reflected by the second reflection region is larger than the particle, at a position of the particle at which the scattered light is generated.

Effects of the Invention

As described above, according to the present invention, efficiency in receiving the scattered light from the particle and accuracy in detecting the particle can be improved.

BRIEF DESCRIPTION OF THE DRAWINGS

FIG. 18 is a block diagram illustrating a detection circuit unit of the micro object detection apparatus according to the third embodiment of the present invention.

MODE FOR CARRYING OUT THE INVENTION

Figure 1:
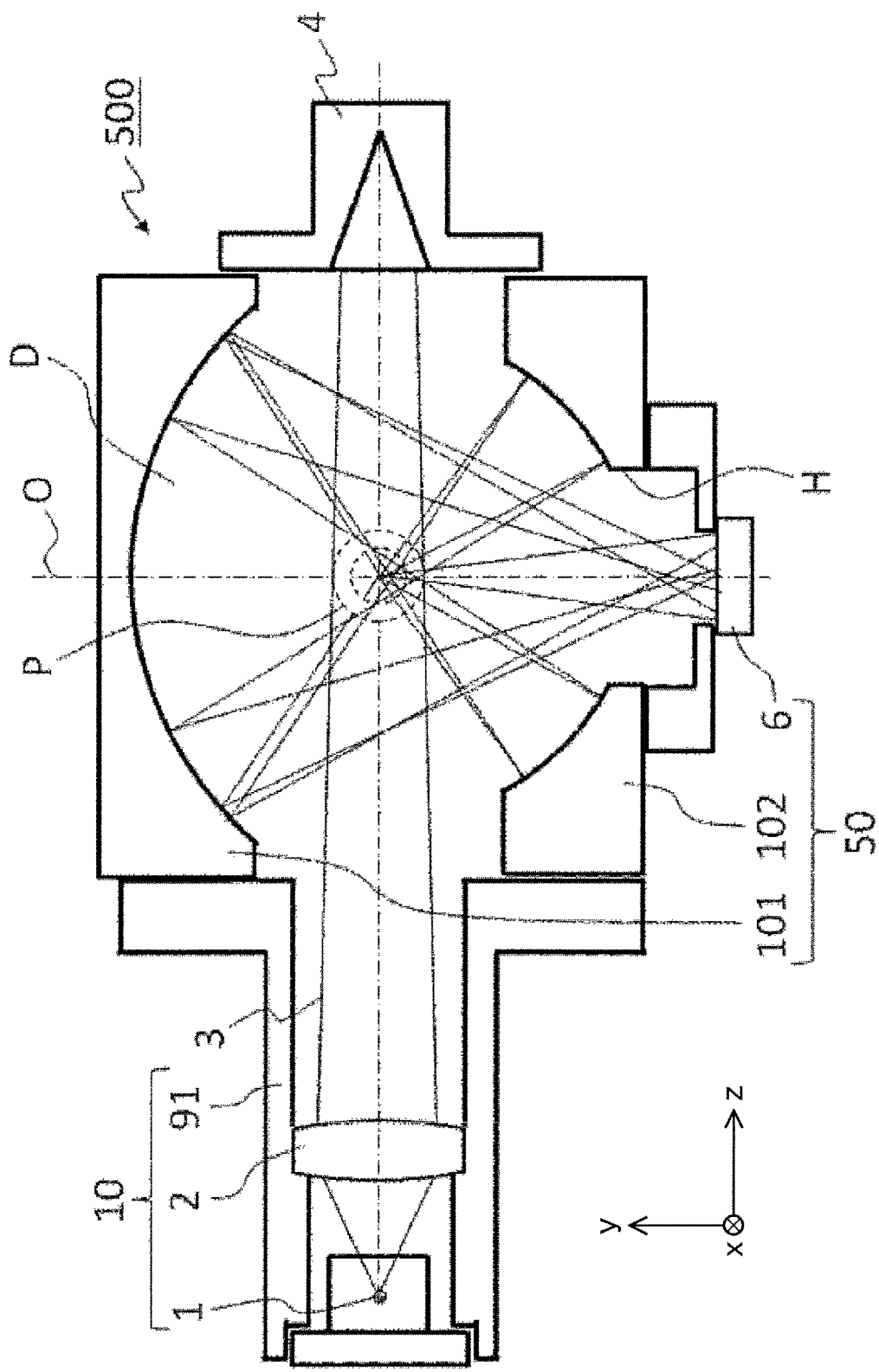
FIG. 1 is a configuration diagram schematically illustrating a configuration of a micro object detection apparatus according to a first embodiment of the present invention.

Regarding matter such as PM2.5 and PM10 also called micro particulate matter, since the light amount of scattered light is small, collecting the scattered light by using a converging mirror is effective for increasing the light amount. On the other hand, as for pollen, dust, or the like, since particle diameters are large, collecting scattered light is less effective than the micro particulate matter.

A patent reference, Japanese Patent Application Publication No. 2004-125602, describes a pollen sensor that measures the intensity of polarized light in a direction parallel to irradiation light from a light emitting unit and the intensity of polarized light in a direction perpendicular to the irradiation light from the light emitting unit, among scattered light from a suspended particle, and distinguishes between a suspended particle of pollen and a suspended particle other than pollen. Moreover, each of light receiving units for receiving the scattered light is located in a direction of scattered light of 60° from the incident light axis of the irradiation light.

However, in an optical system for collecting scattered light by using a converging mirror and the like, when the scattered light is reflected in an oblique direction by the converging mirror, the optical system is affected by change in polarization direction and change in reflectance and it causes reduction in accuracy in detecting polarized light component. Thus, it is difficult to detect micro particulate matter and pollen by using one optical system.

Moreover, for example, in the case of an optical system that uses an elliptical mirror and a spherical mirror as in patent reference 1, a particle at which scattered light is generated is a light blocking object for scattered light reflected by the spherical mirror. By this light blocking of the scattered light, one peak of a detection signal corresponding to one particle is changed into two peaks. Hence, there is a problem that erroneous detection of miscounting the number of particles occurs.

To facilitate explanation, coordinate axes of an xyz-rectangular coordinate system are illustrated in each of the drawings. In the following description, the direction linking the center of a suction port 5a and the center of a discharge port 5b in a micro object detection apparatus 11 is set as an x axis direction. The suction port 5a side is a +x axis direction. The discharge port 5b side is a −x axis direction. The direction linking the center of a first converging mirror 101 and the center of a second converging mirror 102 is set as a y axis direction. The first converging mirror 101 side is a +y axis direction. The second converging mirror 102 side is a −y axis direction. The direction in which irradiation light 3 is radiated is set as a z axis direction. The direction in which the irradiation light 3 travels is a +z axis direction. The side on which a laser light emitting element 1 is located is a −z axis direction.

For example, in the case of patent reference 1, a y axis is parallel to a line segment linking a first focal point and a second focal point of the elliptical mirror. Moreover, the y axis is an axis perpendicular to a z-x plane.

First Embodiment

Figure 2:
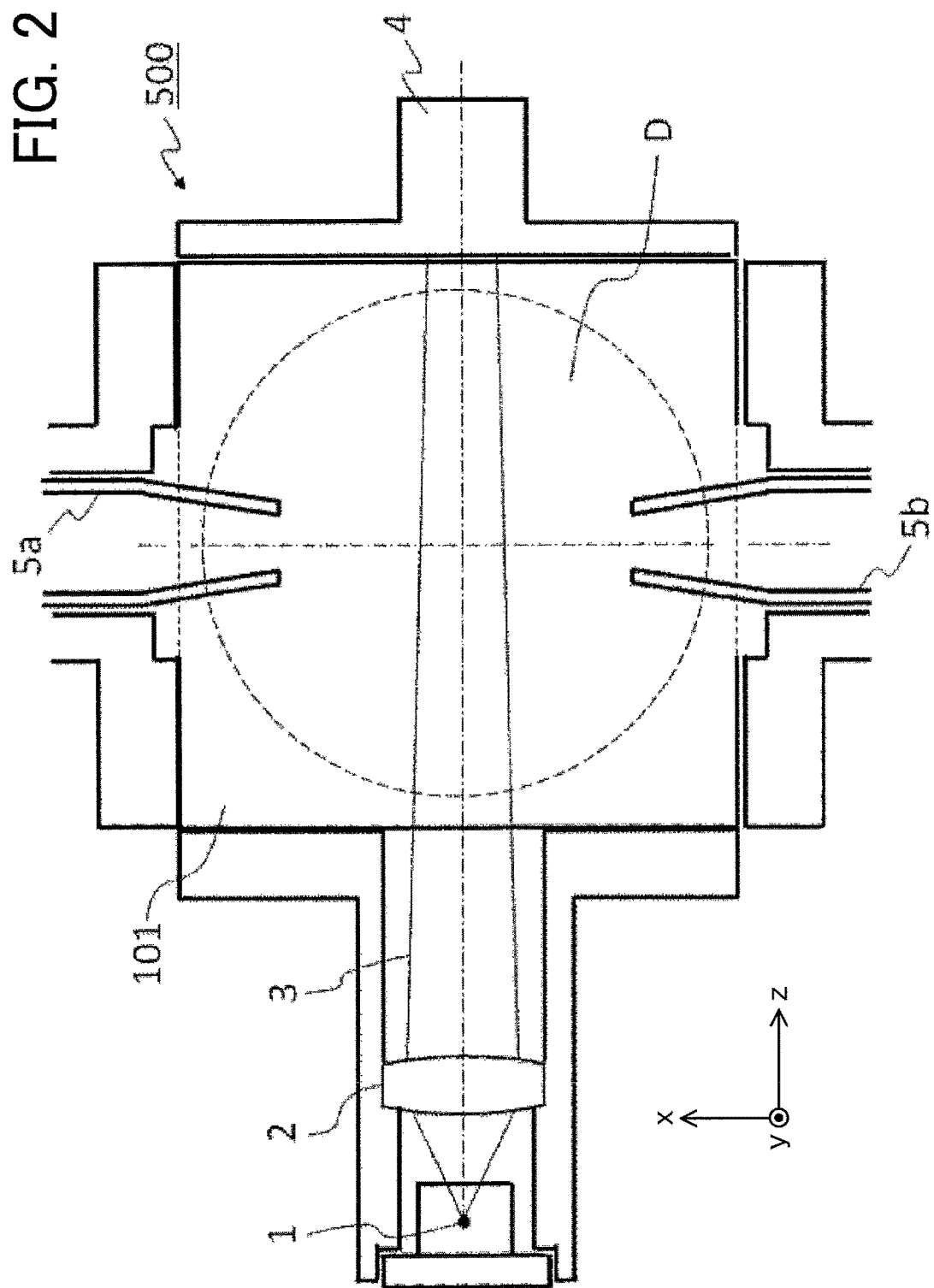
FIG. 2 is a configuration diagram schematically illustrating the configuration of the micro object detection apparatus according to the first embodiment of the present invention.

FIGS. 1 and 2 are configuration diagrams schematically illustrating a configuration of an optical system 500 of a micro object detection apparatus 11 according to a first embodiment of the present invention. FIG. 1 is a configuration diagram illustrating a y-z cross section of the optical system 500 of the micro object detection apparatus 11. FIG. 2 is a configuration diagram illustrating a z-x plane of the optical system 500 of the micro object detection apparatus 11.

<Optical System 500 of Micro Object Detection Apparatus 11>

As illustrated in FIGS. 1 and 2, the optical system 500 of the micro object detection apparatus 11 includes a detection optical system 50 as a main component. The optical system 500 of the micro object detection apparatus 11 can include a laser light emitting element 1 or a lens 2. In addition, the optical system 500 of the micro object detection apparatus 11 can include a beam trap 4 or a radiation unit holder 91.

The detection optical system 50 includes a first converging mirror 101, a second converging mirror 102, and a light reception element 6.

A laser light radiation unit 10 includes the laser light emitting element 1. In addition, the laser light radiation unit 10 can include the lens 2 or the radiation unit holder 91.

The laser light emitting element 1 is a light source. The lens 2 directs light emitted from the laser light emitting element 1 to a detection region D.

In the first embodiment, a light source is described as a laser light source. However, the light source may be an LED or the like, for example. In this case, the irradiation light 3 is LED light or the like. Moreover, the irradiation light 3 may be monochromatic light, or may be white light. The laser light emitting element 1 emits the irradiation light 3.

The lens 2 transmits the light emitted from the laser light emitting element 1, as irradiation light for irradiating a detection target particle R. The lens 2 transmits the irradiation light 3 emitted from the laser light emitting element 1 to the detection region D.

In the first embodiment, the laser light (the irradiation light 3) emitted from the laser light emitting element 1 is incident on the lens 2. The lens 2 converges the entering laser light (the irradiation light 3), for example. Alternatively, the lens 2 converts the entering laser light (the irradiation light 3) to parallel light, for example. The lens 2 changes a divergence angle of the entering laser light (the irradiation light 3).

The laser light (the irradiation light 3) coming from the lens 2 is directed to the detection region D by the lens 2. The laser light (the irradiation light 3) directed to the detection region D is in a converged light state or a parallelized light state, for example. The lens 2 may be a cylindrical lens or a toroidal lens that has a light converging function, for example.

The suspended particle R exists in the detection region D. The lens 2 can be removed in a case such as when the intensity of the irradiation light 3 can be set sufficiently large for the detection of the suspended particle R.

The radiation unit holder 91 holds the laser light emitting element 1 and the lens 2, for example. The radiation unit holder 91 combines the laser light emitting element 1 and the lens 2 as one unit.

The radiation unit holder 91 is attached to the first converging mirror 101 or the second converging mirror 102, for example. In FIG. 1, the radiation unit holder 91 is attached to the first converging mirror 101 and the second converging mirror 102, for example.

The particle R is micro particulate matter suspended in the air, as described above. The suspended particle R of the detection target includes pollen, dust, cigarette smoke, or the like. The particle R is pollen, dust, or the like, for example. The dust is referred to as house dust. In addition, the particle R includes dead bodies, their broken pieces and excretion of minute creatures such as mites, and the like. In addition, the particle R includes what is called micro particulate PM2.5, micro particulate matter PM10, or the like. PM2.5 is a small particle having a particle size of 2.5 μm or less, among small particles suspended in the air. The ingredients of PM2.5 include inorganic elements, such as carbon, nitrate, sulfate, ammonium salt, silicon, sodium, or aluminum. PM10 is a small particle having a particle size of 10 μm or less, among small particles suspended in the air.

PM2.5 and PM10 are also referred to as micro particulate matter. The "particulate matter" means micrometer-size solid or liquid fine particles.

The particle R is irradiated with the irradiation light 3. In this case, scattered light L is generated from the particle R.

The "scattered light" is light generated when the irradiation light 3 hits the suspended particle R and its propagation state is changed. The "propagation" means that a wave spreads in a medium. Here, the "propagation" means that light travels in a space. The term space means, as described above, in the air, in a liquid, in a vacuum, or the like. However, the "scattered light" includes fluorescence of the suspended particle R generated by the wavelength of the irradiation light 3.

The detection target particle R is not limited particularly, if it is minute matter that generates the scattered light L when irradiated with the irradiation light 3.

The detection optical system 50 includes the first converging mirror 101, the second converging mirror 102, and the light reception element 6. The detection optical system 50 is also referred to as a scattered light receiving unit.

The first converging mirror 101 and the second converging mirror 102 direct part of the scattered light L to the light reception element 6. The first converging mirror 101 is an elliptical mirror, for example. The second converging mirror 102 is a spherical mirror, for example. The first converging mirror 101 and the second converging mirror 102 may be regions that are part of one converging mirror.

Here, the elliptical mirror is not needed to have an ideal ellipsoidal shape. Here, the elliptical mirror is a mirror having a function for collecting light that diffuses from a certain point to another point by its reflection, and is an elliptical mirror in a broad sense. Note that the other point to which the light is collected may be an area having a certain size.

A light beam that passes through one focal point of two focal points of an ellipse is reflected by an elliptical surface, and passes through the other focal point. The elliptical surface is a quadric surface whose cross-section cut by a plane parallel to three coordinate planes is always an ellipse.

The first converging mirror 101 reflects scattered light 111*a* that is incident directly from the particle R, to direct the scattered light to the light reception element 6, by utilizing the positions of the two focal points of the ellipse. For example, the suction port 5*a* and the discharge port 5*b* guide the particle R to the position of one focal point (a first focal point) of the first converging mirror 101. The light reception element 6 is located at the position of the other focal point (a second focal point) of the first converging mirror 101.

The irradiation light 3 hits the particle R in the region of the one focal point (the first focal point). The region in which the irradiation light 3 crosses the passage region P includes the first focal point of the first converging mirror 101.

The light reception element 6 detects the intensity of the scattered light L. That is, the light reception element 6 is a light detector. The light reception element 6 is a photo diode or the like, for example.

The light reception element 6 outputs an electric current or voltage corresponding to the intensity of the light. The light reception element 6 includes a light reception region for receiving the light. The light reception element 6 receives the scattered light L.

When the output of the light reception element 6 is an electric current, the micro object detection apparatus 11 can include an IV conversion circuit (current-voltage conversion circuit) for converting a current value to voltage, at a stage subsequent to the light reception element 6.

On the other hand, when the output of the light reception element 6 is voltage, the micro object detection apparatus 11 can include a buffer circuit at the stage subsequent to the light reception element 6, in order to convert the voltage to stable voltage. The buffer circuit is a voltage follower or the like, for example.

The suction port 5*a* is a suction nozzle, for example. The discharge port 5*b* is a discharge nozzle, for example. The suction port 5*a* guides the air or a liquid test object containing the detection target particle R to the detection region D. Moreover, the discharge port 5*b* discharges the air or a liquid test object containing the detection target particle R from the detection region D. The passage region P where the particle R passes through is formed between the suction port 5*a* and the discharge port 5*b*.

Note that the irradiation light 3 radiated from the laser light emitting element 1 is needless to be orthogonal to a straight line that passes through the suction port 5*a* and the discharge port 5*b*, for example. That is, the irradiation light 3 radiated from the laser light emitting element 1 is needless to be orthogonal to the direction in which the particle R flows from the suction port 5*a* to the discharge port 5*b*. That is, the irradiation light 3 radiated from the laser light emitting element 1 can be radiated on the particle R at an inclined angle relative to the direction in which the particle R flows from the suction port 5*a* to the discharge port 5*b*.

The liquid test object refers to a liquid that contains the detection target particle R.

The detection region D is the region surrounded by the first converging mirror 101 and the second converging mirror 102.

For example, the detection region D is a region in a gas, such as air. Alternatively, the detection region D is a region in a liquid, such as water. Alternatively, the detection region D is a vacuum region.

The detection target particle R passes through the detection region D. In the first embodiment, the particle R passes through the detection region D from the +X axis side toward the −X axis side. For example, the particle R is suspended in the air. Alternatively, the particle R is contained in the liquid.

The particle R passage region P in the detection region D may be a region closed by a wall or the like that allows the irradiation light 3 to transmit. Alternatively, the passage region P where the particle R passes through in the detection region D may be an open region.

That is, the irradiation light 3 passes through the wall that surrounds the passage region P. The passage region P is a region through which the particle R passes from entering the detection region D until exiting the detection region D. In the first embodiment, the particle R enters the detection region D from the suction port 5a. The particle R exits the detection region D from the discharge port 5b.

The beam trap 4 prevents the irradiation light 3 that has exited the passage region P where the particle R passes through from being reflected and returning to the passage region P. The beam trap 4 traps light, absorbs light, or releases light to the outside of the detection region D.

That is, the beam trap 4 transmits light to the outside of the detection region D. The beam trap 4 prevents light from entering the detection region D again.

<Relationship Between Scattered Light L and Light Reception Element 6>

A relationship between the scattered light L and the light reception element 6 in the detection region D in the micro object detection apparatus 11 according to the first embodiment will be described.

In the detection optical system 50 of the micro object detection apparatus 11 according to the first embodiment, there are three types of paths leading the scattered light L generated at the particle R to the light reception element 6.

The scattered light L is generated at the particle R. The scattered light L is directed to the light reception element 6 by the detection optical system 50. There are three types of paths to the light reception element 6.

Figure 3:
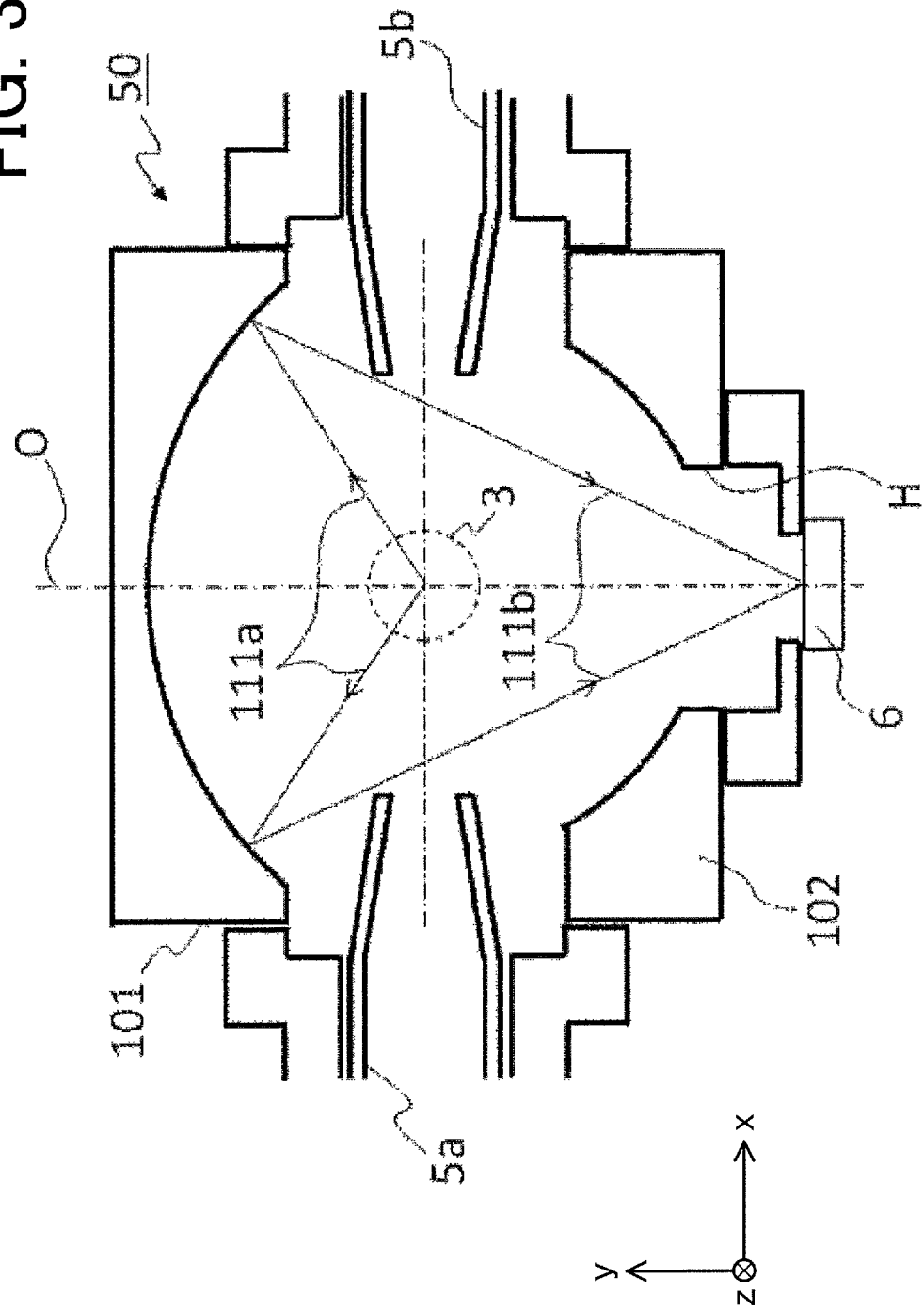
FIG. 3 is a diagram schematically illustrating a light beam on a first path in the micro object detection apparatus according to the first embodiment of the present invention.
Figure 4:
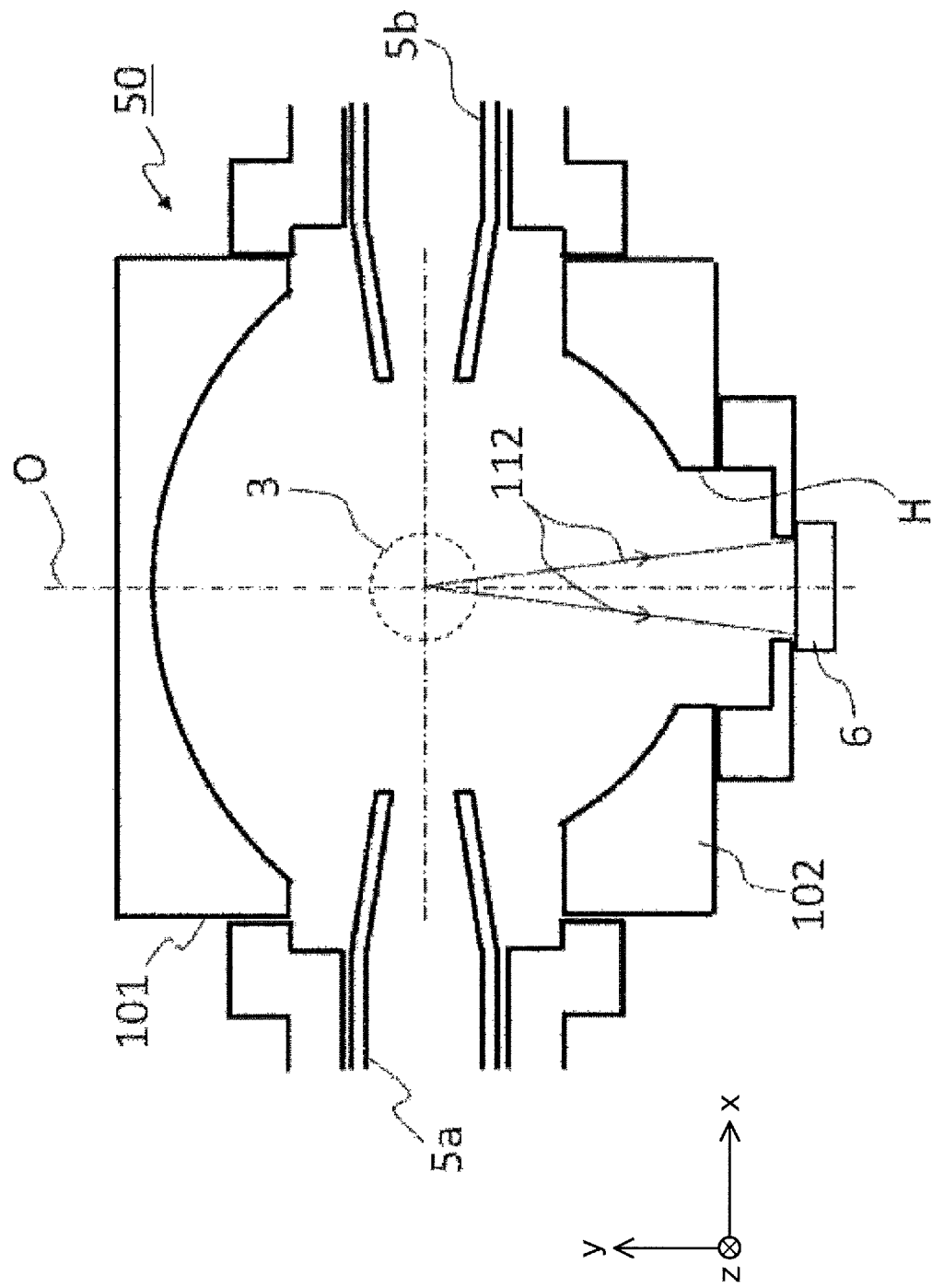
FIG. 4 is a diagram schematically illustrating a light beam on a second path in the micro object detection apparatus according to the first embodiment of the present invention.
Figure 5:
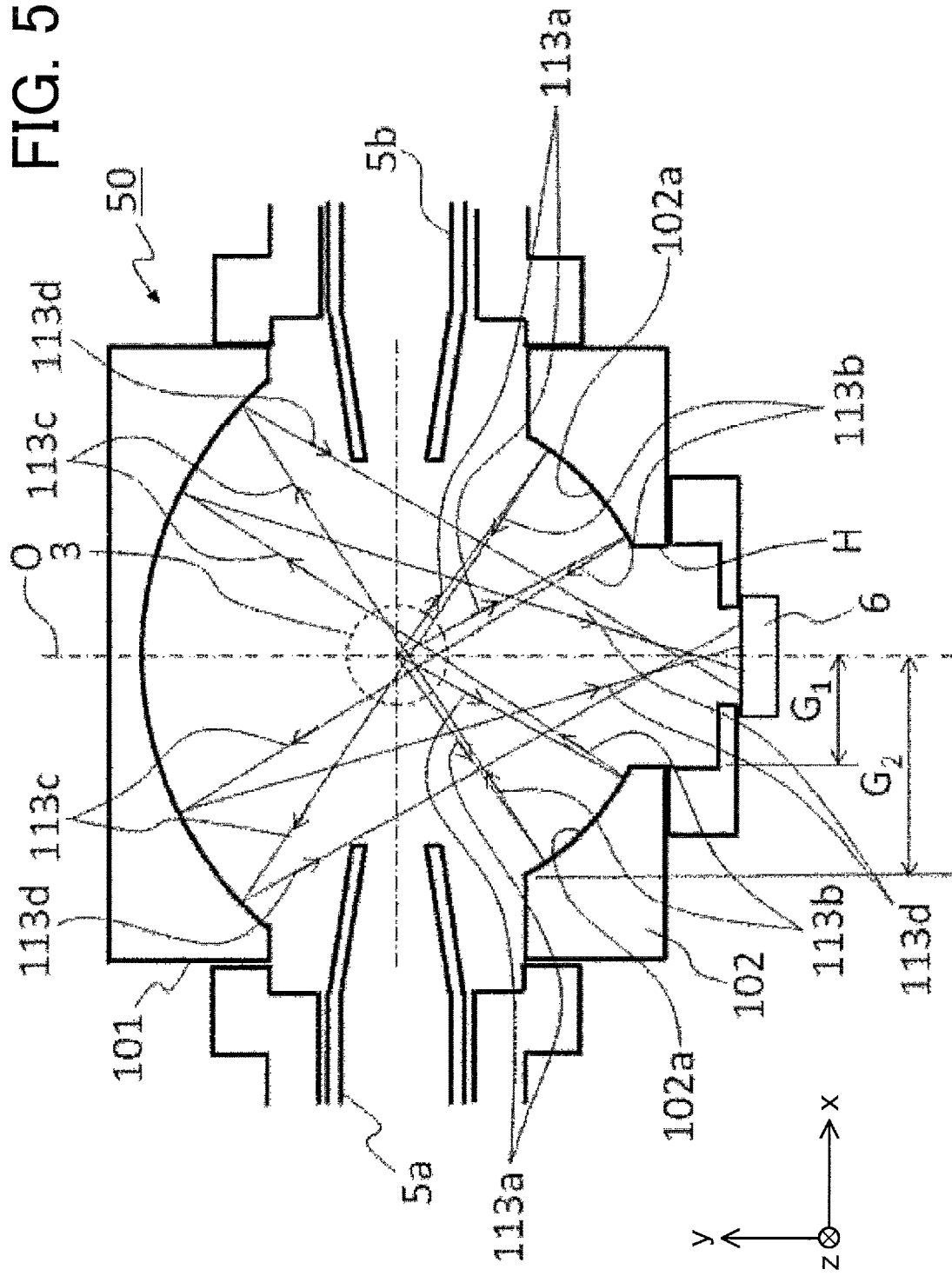
FIG. 5 is a diagram schematically illustrating a light beam on a third path in the micro object detection apparatus according to the first embodiment of the present invention.

FIGS. 3, 4, and 5 are diagrams schematically illustrating the paths of the light beam in the micro object detection apparatus 11. FIG. 3 illustrates a first path. FIG. 4 illustrates a second path. FIG. 5 illustrates a third path. FIGS. 3, 4, and 5 illustrate only representative light beams of the scattered light L, to reduce the complexity of the drawings.

In FIG. 3, the scattered light L (a light beam 111a) scattered by the particle R reaches the first converging mirror 101. When reaching the first converging mirror 101, the scattered light L (the light beam 111a) is reflected by the first converging mirror 101. After the reflection by the first converging mirror 101, the scattered light L (a light beam 111b) reaches the light reception element 6. In the following, this path is referred to as the first path. The scattered light L represented as the first path is referred to as the light beams 111a, 111b.

FIG. 3 illustrates the behavior of the light beams, by using the light beams 111a, 111b that are representative light beams of the scattered light L. The light beam 111a is a light beam of the scattered light L from the particle R and is incident on the first converging mirror 101. The light beam 111b is a light beam of reflected light obtained when the light beam 111a is reflected by the first converging mirror 101. The reflected light 111b is directed to the light reception element 6.

In FIG. 4, the scattered light L (the light beam 112) scattered by the particle R reaches the light reception element 6 directly. That is, the scattered light L (the light beam 112) is not reflected by the first converging mirror 101 or the second converging mirror 102. In the following, this path is referred to as the second path.

FIG. 4 illustrates the behavior of the light beam, with the light beam 112 that is a representative light beam of the scattered light L. The light beam 112 is a light beam of the scattered light L that directly reaches the light reception element 6 from the particle R. Thus, the light beam 112 reaches the light reception element 6, without reaching the first converging mirror 101 or the second converging mirror 102.

In FIG. 5, the scattered light L (light beam 113a) scattered at the particle R reaches the second converging mirror 102. The scattered light L (light beam 113a) that has reached the second converging mirror 102 is reflected by the second converging mirror 102. The scattered light L (light beam 113b) reflected by the second converging mirror 102 reaches the first converging mirror 101. The scattered light L (light beam 113c) that has reached the first converging mirror 101 is reflected by the first converging mirror 101. Note that the light beam 113c is the same light beam as the light beam 113b. The scattered light L (light beam 113d) reflected by the first converging mirror 101 reaches the light reception element 6. In the following, this path is referred to as the third path.

FIG. 5 illustrates the behavior of the light beams, by using the light beams 113a, 113b, 113c, and 113d that are representative light beams of the scattered light L. The light beam 113a is a light beam of the scattered light L that travels toward the second converging mirror 102 from the particle R. The light beam 113b is a light beam of reflected light obtained when the light beam 113a of the scattered light L is reflected by the second converging mirror 102. The light beam 113c is a light beam when the reflected light 113b is incident on the first converging mirror 101. That is, the light beam 113c and the light beam 113b are the same light beam. The light beam 113d is a light beam of reflected light obtained when the light beam 113c is reflected by the first converging mirror 101. The light beam 113d is directed to the light reception element 6. In the following, the light beams 113b, 113d are also referred to as reflected light.

That is, the light beams 113a, 113b, 113c, and 113d can be described as below. The light beam 113a is the light beam that reaches the second converging mirror 102 from the particle R. The light beam 113b is the light beam that is reflected by the second converging mirror 102 and reaches the passage region P. That is, the light beam 113b is the light beam that returns to the original position of the particle R from the second converging mirror 102. The light beam 113c is the light beam that reaches the first converging mirror 101 from the passage region P. The light beam 113d is the light beam that is reflected by the second converging mirror 102 and reaches the light reception element 6.

The above configuration of the detection optical system 50 of the micro object detection apparatus 11 according to the first embodiment differs from the configuration disclosed in prior reference 1. The shape of the second converging mirror 102 according to the first embodiment proactively generates aberration at the focal point position, unlike the shape of the spherical mirror disclosed in prior reference 1.

The light flux diameter of the scattered light reflected by the second converging mirror 102 is larger than the particle diameter of the particle R, at the position of the particle R at which the scattered light is generated.

The light flux diameter of the scattered light reflected by the second converging mirror 102 is larger than the light flux diameter of the scattered light reflected by the converging mirror in the case of the second converging mirror 102 having a spherical shape, at the position of the particle R at which the scattered light is generated. The second converging mirror 102 is an aspherical mirror based on this spherical shape, for example. The spherical shape approximates the aspherical shape of the second converging mirror 102, for example. The second converging mirror 102 generates a plurality of focal points and disperses those focal points, for example. Moreover, the second converging mirror 102 generates spherical aberration, for example. The second converging mirror 102 generates larger aberration than aberration that remains when manufactured as a spherical mirror, for example.

In general, the concentrated light has the spherical aberration smaller than 0.07 λrms, for example. Hence, the collected light collected by the second converging mirror 102 has the spherical aberration equal to or larger than 0.07 λrms.

Moreover, the shape of the second converging mirror 102 is the shape that proactively generates the aberration at the focal point position. Hence, the shape of the second converging mirror 102 is an aspherical shape, for example. That is, the spherical shape of the second converging mirror 102 is changed to the aspherical shape.

Then, the aberration generated by the second converging mirror 102 is larger than the aberration generated by the spherical mirror that approximates the aspherical shape of the second converging mirror 102. That is, the second converging mirror 102 generates larger aberration than the aberration generated by the original spherical mirror.

This second converging mirror is different, and thereby the efficiency in detecting the scattered light L improves, as described later. Moreover, the accuracy in detecting number concentration or weight concentration of the particle R can be improved. The "number concentration" represents the number of particles per unit volume. The "weight concentration" represents the weight of particles per unit volume.

<Type of Scattered Light>

Figure 6:
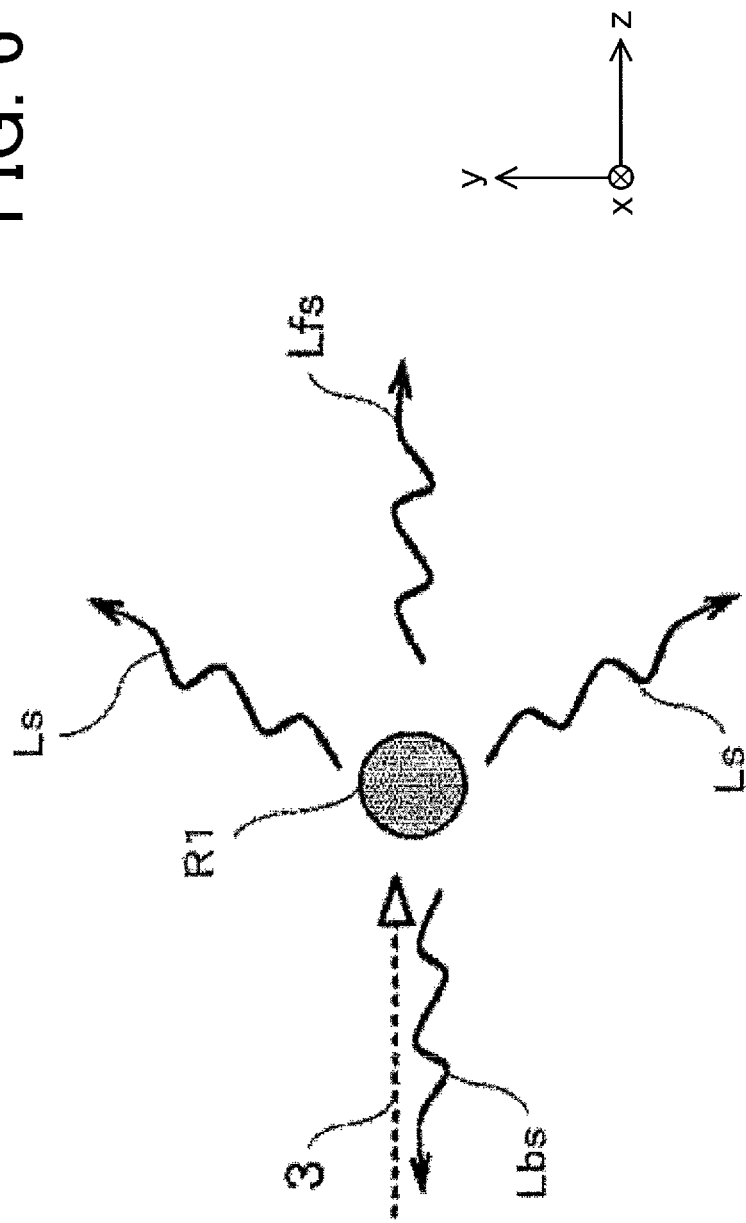
FIG. 6 is a diagram schematically illustrating main scattered light generated when a particle is irradiated with laser light.

FIG. 6 is a diagram schematically illustrating main scattered light L generated when the particle R is irradiated with the irradiation light 3. The irradiation light 3 is laser light, for example.

The irradiation light 3 is light emitted from the laser light emitting element 1, in the first embodiment. The scattered light L is light scattered when the irradiation light 3 hits the particle R.

Scattered light Lbs is light traveling toward the direction (−z axis direction) of the laser light emitting element 1. The scattered light Lbs is light (returning light) returning in the direction (−z axis direction) of the laser light emitting element 1. That is, the scattered light Lbs is light traveling backward. The "backward" means the opposite direction (−z axis direction) to the direction in which the light is emitted from the laser light emitting element 1 (+z axis direction).

Scattered light Lfs is light traveling forward (+z axis direction). The "forward" means the direction in which the light is emitted from the laser light emitting element 1 (+z axis direction).

Scattered light Ls is light traveling laterally. The "laterally" means a direction perpendicular to the direction (+z axis direction) in which the light is emitted from the laser light emitting element 1. That is, the "laterally" means a direction on a plane (x-y plane) perpendicular to the direction (+z axis direction) in which the light is emitted from the laser light emitting element 1. However, the traveling direction of the light beam may incline relative to the z axis. The scattered light Ls illustrated in FIG. 6 travels with an inclination in the +z axis direction.

That is, the scattered light Ls is light that travels with an inclination to the direction in which the irradiation light 3 travels. For example, assuming that the irradiation light 3 travels along the axis of a cylinder, the scattered light Ls is a light beam that passes through the side surface of the cylinder. Here, the cylinder used in the description is an imaginary cylinder. Laterally means a direction other than forward and backward.

The light beams 111a, 112, 113a illustrated in FIGS. 3, 4, and 5 are the scattered light Ls.

Here, explanation of general scattering will be given. In general, when the particle R is irradiated with the irradiation light 3 having a wavelength comparatively close to the size of the particle R, the scattered light L is generated. The irradiation light 3 is not limited to laser light particularly The scattered light L is roughly classified into two types of light. One is the forward scattered light Lfs. The other is scattered light other than the forward scattered light Lfs. The forward scattered light Lfs is generated in a direction in which the irradiation light 3 propagates (+z axis direction). The scattered light L generated in a direction other than the direction in which the irradiation light 3 propagates is, for example, the backward scattered light Lbs or the lateral scattered light Ls.

The proportion of the intensity of the scattered light L changes, according to the shape and the size of the particle R. The intensity distribution (distribution of the scattering intensity) of the scattered light traveling from the particle R toward each direction changes, according to the shape and the size of the particle R.

For example, as the size (for example, diameter) of the particle R becomes larger, the intensity of the scattered light L becomes greater. The intensity of the scattered light L is far smaller than the intensity of the irradiation light 3. As part of the scattered light L, there is the backward scattered light Lbs traveling toward the direction (−z axis direction) opposite to the traveling direction of the irradiation light 3 (+z axis direction).

<Detection Circuit Unit 60>

Figure 7:
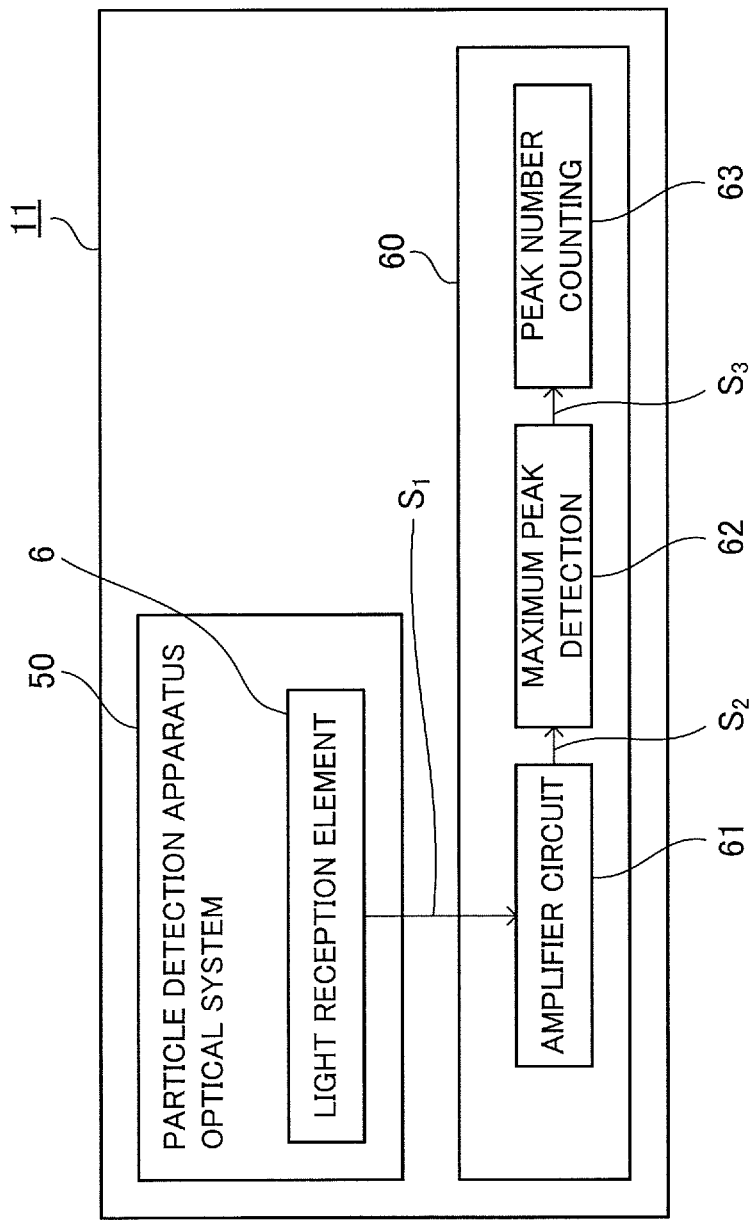
FIG. 7 is a block diagram illustrating a detection circuit unit of the micro object detection apparatus according to the first embodiment of the present invention.

Next, the configuration other than the detection optical system 50 will be described. FIG. 7 is a block diagram illustrating a detection circuit unit 60 of the micro object detection apparatus 11 according to the first embodiment of the present invention.

The micro object detection apparatus 11 according to the first embodiment can employ the detection circuit unit 60. The detection circuit unit 60 is effective to prevent a negative effect of quasi peak described later. However, when the quasi peak is prevented by the detection optical system 50 described in the first embodiment, it is not necessary for the micro object detection apparatus 11 to use the detection circuit unit 60. On the other hand, the detection circuit unit 60 is effective when used in a conventional detection optical system 51.

Note that a current-voltage conversion unit for converting an output current value from the light reception element 6 to a voltage value will be omitted here.

The detection circuit unit 60 includes a peak number counter 63. The detection circuit unit 60 can include an amplifier circuit 61 or a maximum peak detector 62.

The amplifier circuit 61 amplifies or attenuates the level of an output signal $S_1$ from the light reception element 6. The amplifier circuit 61 outputs a signal $S_2$. The amplifier circuit 61 can be removed when a sufficient signal level is satisfied in the subsequent processing, for example.

The signal $S_2$ is obtained by amplifying or attenuating the level of the output signal $S_1$.

The maximum peak detector 62 receives the output signal $S_2$. The maximum peak detector 62 detects a maximum peak point of the output signal $S_2$ from the amplifier circuit 61. The maximum peak point of the output signal $S_2$ corresponds to the particle R. The maximum peak detector 62 sequentially processes the detection of the maximum peak point of the output signal $S_2$. Note that the maximum peak detector 62 can be removed when the number of particles R can be counted by using a threshold value or the like, without detecting the maximum peak point, for example.

The maximum peak detector 62 outputs a signal $S_3$. The signal $S_3$ indicates the maximum peak point of the output signal $S_2$.

The peak number counter 63 receives the signal $S_3$ indicating the maximum peak point output by the maximum peak detector 62. The peak number counter 63 counts the number of peaks corresponding to the detection of the particle R. The peak number counter 63 is the counter that counts the number of peaks of the signal $S_3$. Alternatively, the peak number counter 63 is a particle number counter that counts the number of particles by counting the number of peaks of the signal $S_3$.

The number concentration or the weight concentration of the particles R can be calculated by using the count value of the number of peaks obtained by the peak number counter 63 of the detection circuit 60. The micro object detection apparatus 11 calculates the number concentration or the weight concentration of the particles R, by using the count value of the number of peaks.

<Feature and Effect of Second Converging Mirror 102>

Next, features and effects of the second converging mirror 102 in the micro object detection apparatus 11 according to the first embodiment will be described.

A conventional micro object detection apparatus will be described by using FIGS. 8 and 9, in order to describe the features of the second converging mirror and resulting effects in the micro object detection apparatus 11 according to the first embodiment.

Figure 8:
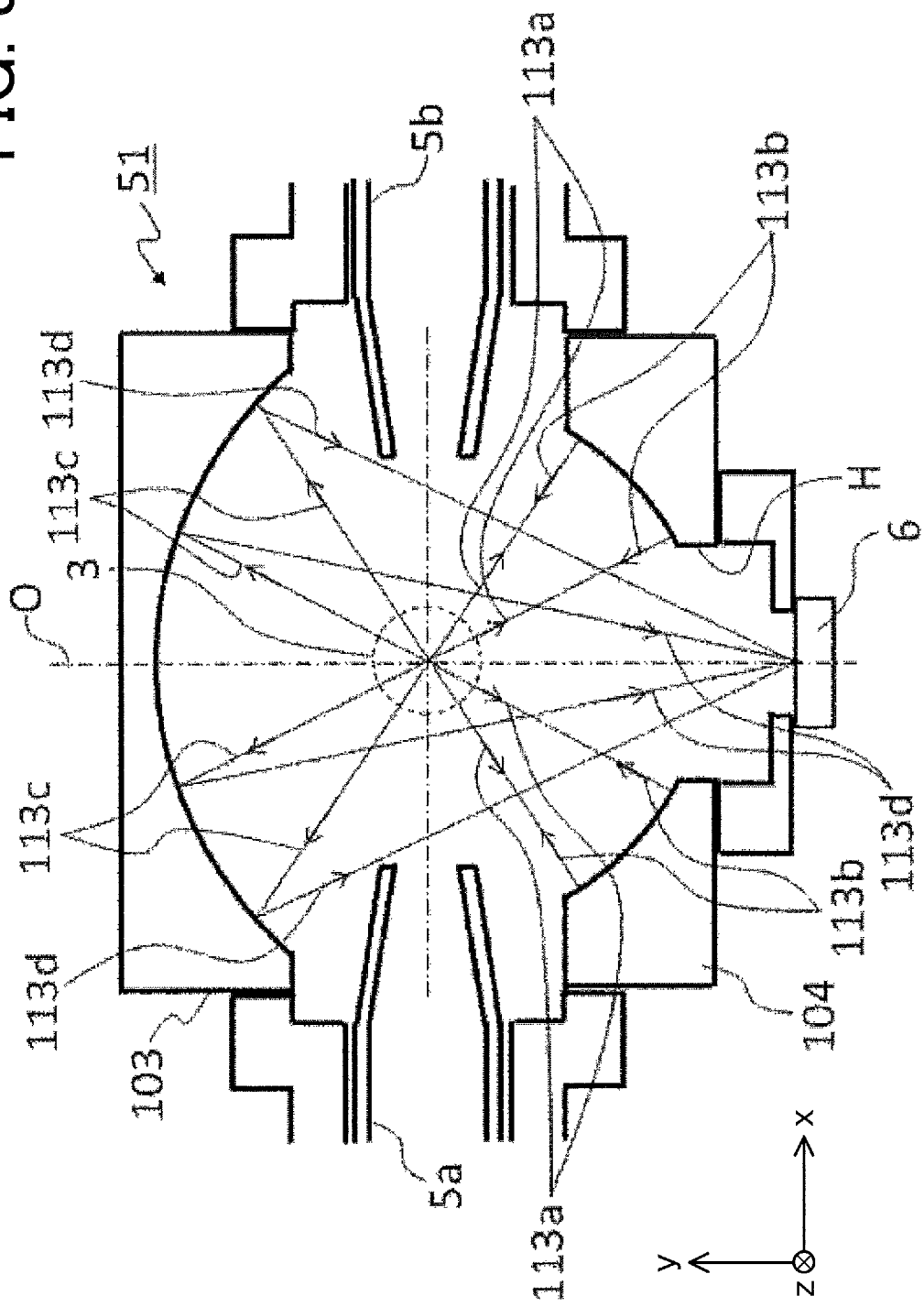
FIG. 8 is a diagram schematically illustrating a light beam on a third path in a conventional micro object detection apparatus.

FIG. 8 is a diagram schematically illustrating a light beam on a third path in the detection optical system 51 of the conventional micro object detection apparatus. FIG. 9 is a diagram schematically illustrating a waveform of a detection signal $S_1$ of the conventional micro object detection apparatus. FIG. 10 is a diagram schematically illustrating a waveform of the detection signal $S_1$ of the micro object detection apparatus 11 according to the first embodiment.

FIG. 8 corresponds to FIG. 5 illustrating the micro object detection apparatus 11. Thus, the same reference signs are assigned the same components and light beams as in FIG. 5. The description of FIG. 5 is substituted for the description of them.

Figure 9:
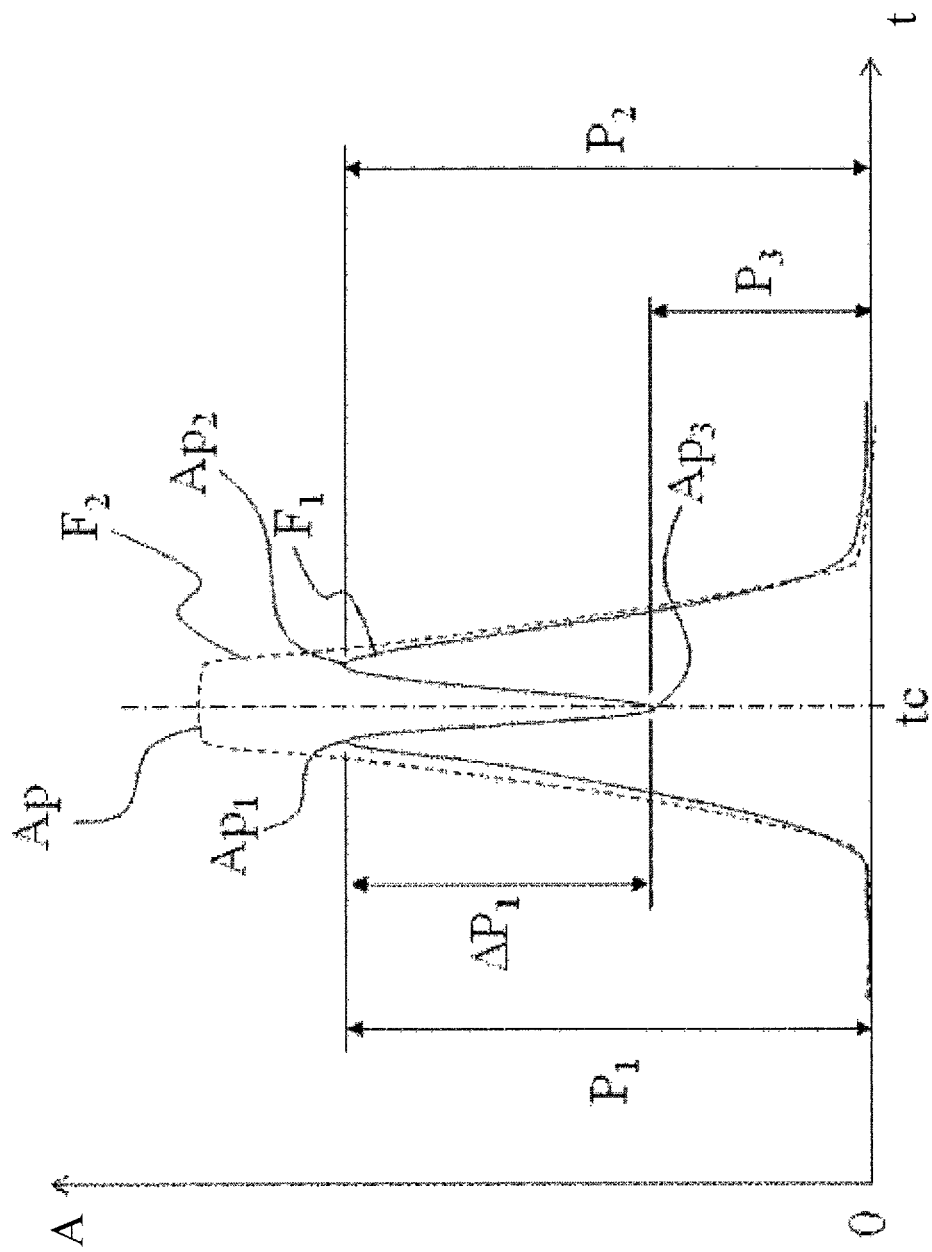
FIG. 9 is a diagram schematically illustrating a waveform of a detection signal in the conventional micro object detection apparatus.
Figure 10:
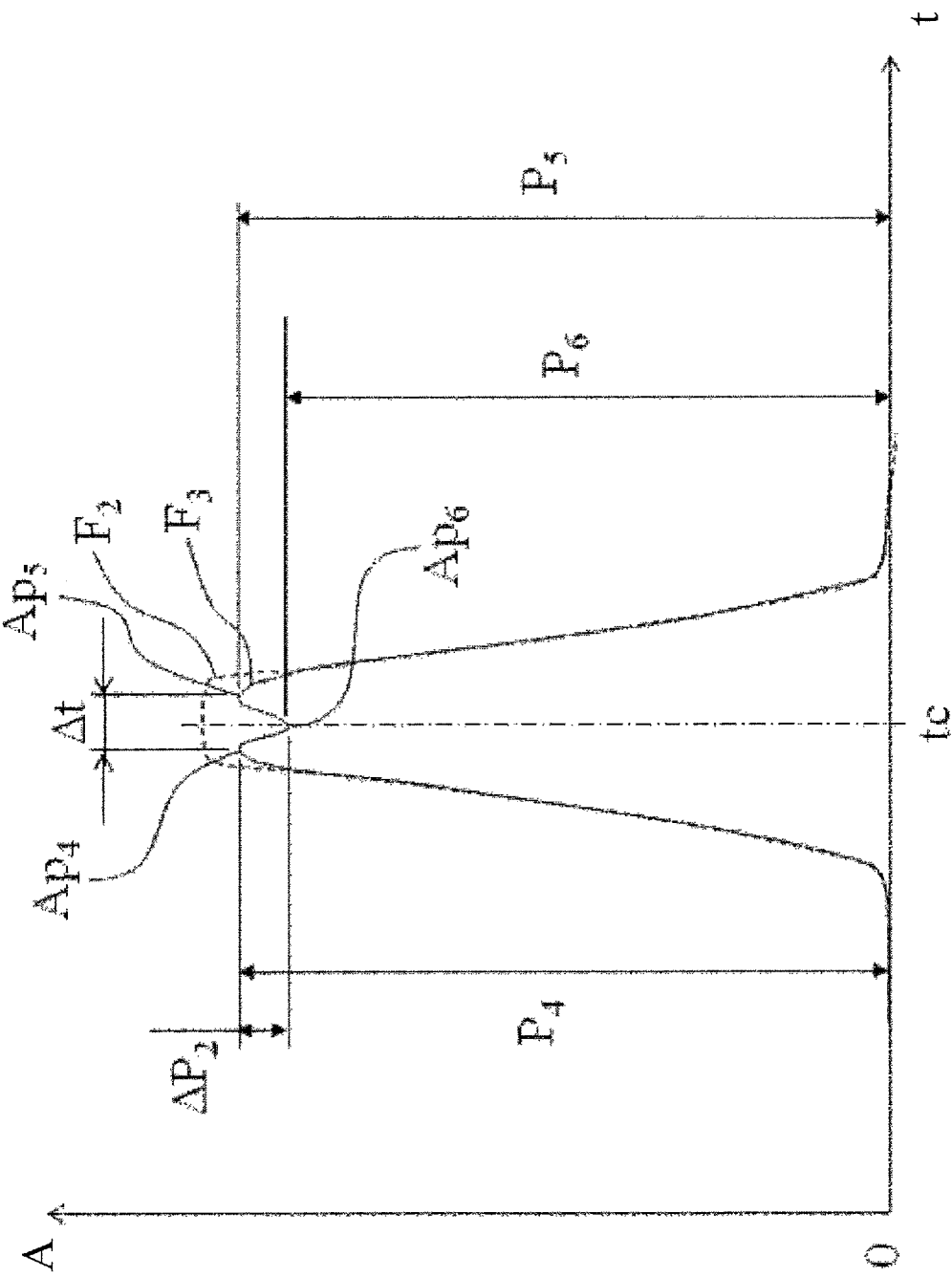
FIG. 10 is a diagram schematically illustrating a waveform of a detection signal $S_1$ in the micro object detection apparatus according to the first embodiment of the present invention.

In FIGS. 9 and 10, the vertical axis represents output values A of the detection signal $S_1$, and the horizontal axis represents time (msec).

The conventional micro object detection apparatus differs from the micro object detection apparatus 11 according to the first embodiment, in the shape and the function of the second converging mirror 102.

That is, the conventional micro object detection apparatus differs from the micro object detection apparatus 11 according to the first embodiment, in the shape of the second converging mirror 102. In addition, the conventional micro object detection apparatus differs from the micro object detection apparatus 11 according to the first embodiment, in the function of the second converging mirror 102.

In the second converging mirror 104 according to the conventional micro object detection apparatus, the reflection surface has a spherical shape. The focal point of the second converging mirror 104 according to the conventional micro object detection apparatus is identical with one focal point (the first focal point) of the first converging mirror 103. As described above, the particle R is guided to the position of the first focal point.

As described above, the first converging mirror 103 is an elliptical mirror. For example, the first converging mirror 103 has the shape of a spheroid. The elliptical mirror is a mirror surface having a surface that reflects the light radiated from one focal point (the first focal point) to collect the light into the other focal point (the second focal point) by utilizing two focal points that are characteristics of an ellipse.

The scattered light L (the light beam 113a) scattered at the particle R reaches the second converging mirror 104. The scattered light L (the light beam 113a) that has reached the second converging mirror 104 is reflected by the second converging mirror 104. Then, the scattered light L (the light beam 113b) reflected by the second converging mirror 104 returns to the position of the first focal point (the position of the particle R) again.

Hence, the reflected light 113b of the second converging mirror 104 travels the completely same path as the first path. The first path is a path for a light beam of the scattered light L generated at the particle R that is incident on the first converging mirror 103 and then directed to the light reception element 6. The light beam of the scattered light L generated at the particle R that is incident on the first converging mirror 103 and then directed to the light reception element 6 is the light beams 111a, 111b illustrated in FIG. 3.

Thereby, the detection optical system 51 can collect both of the scattered light L on the third path and the scattered light L on the first path, at the light receiving surface of the light reception element 6.

However, when the particle R passes through the position of the focal point of the second converging mirror 104, the particle R itself becomes a light blocking object on the third path. That is, the light beam 113b reflected by the second converging mirror 104 is blocked by the particle R. Thus, the detection optical system 51 is unable to direct the scattered light L blocked by the particle R, to the light reception element 6. This decreases the efficiency in detecting the scattered light L from the particle R. In addition, the accuracy in detecting the particle R in the detection circuit unit 60 decreases.

The scattered light L blocked by the particle R sometimes travels in a direction other than the reflection surface of the first converging mirror 103 and the second converging mirror 104, for example. An example is the direction of the suction port 5a or the discharge port 5b. Another example is the direction of the laser light emitting element 1 or the beam trap 4.

FIG. 9 is a diagram schematically illustrating a waveform $F_1$ of the detection signal $S_1$ when one particle R passes through the position of the focal point, in the case of the conventional micro object detection apparatus. The waveform $F_1$ of the detection signal $S_1$ in the case of the conventional micro object detection apparatus is indicated by a solid line in FIG. 9. A waveform $F_2$ of an ideal detection signal is indicated by dashed line in FIG. 9.

The particle R itself blocks the scattered light L, and thereby the signal $S_1$ drops at the center (t=tc) of the waveform $F_1$ of the detection signal $S_1$.

Moreover, the waveform $F_2$ indicated by the dashed line in FIG. 9 is the detection signal $S_1$ obtained when the scattered light L generated at the particle R is ideally detected without being influenced by blocking the particle R. In the waveform $F_2$ of the ideal detection signal $S_1$, one maximum peak point Ap corresponds to one particle.

On the other hand, in the waveform $F_1$ of the detection signal $S_1$ indicated by the solid line in FIG. 9, there are two maximum peak points $Ap_1$, $Ap_2$ for one particle R. There is a minimum peak point $Ap_3$ at which the output value decreases, between the two maximum peak points $Ap_1$, $Ap_2$. In this case, a problem of an error in the number of counts arises when the number of peaks is counted by the detection circuit unit 60 illustrated in FIG. 7, for example.

That is, the detection circuit unit 60 miscounts one particle R as two particles. The detection circuit unit 60 counts one particle R at the maximum peak point $Ap_1$. In addition, the detection circuit unit 60 counts one particle R at the maximum peak point $Ap_2$. A plurality of peak signals are thus generated with respect to one particle R when light is blocked, for example, and such peak signals are referred to as quasi peaks.

The maximum peaks $Ap_1$, $Ap_2$ and the minimum peak point $Ap_3$ are the extreme values of the input signal $S_2$ corresponding to the particle (R). The maximum peaks $Ap_1$, $Ap_2$ are the local maximum values of the input signal $S_2$ corresponding to the particle (R). The minimum peak point $Ap_3$ is the local minimum value of the input signal $S_2$ corresponding to the particle (R). When the input signal $S_2$ is a continuous function, a point at which the input signal $S_2$ changes from increasing to decreasing is referred to as local maximum. Moreover, a point at which the input signal $S_2$ changes from decreasing to increasing is referred to as local minimum. The value of the input signal $S_2$ at a local maximum is a local maximum value. The value of the input signal $S_2$ at a local minimum is a local minimum value.

In FIG. 9, the output value at the maximum peak point $Ap_1$ is a peak value $P_1$. Moreover, the output value at the maximum peak point $Ap_2$ is a peak value $P_2$. Moreover, the output value at the minimum peak point $Ap_3$ is a peak value $P_3$. The difference between the peak values $P_1$, $P_2$ and the peak value $P_3$ is a value $\Delta P_1$.

In contrast, a waveform $F_3$ of the detection $S_1$ in the micro object detection apparatus 11 according to the first embodiment will be described.

FIG. 10 is a diagram schematically illustrating a waveform $F_3$ of the detection signal $S_1$ when one particle R passes through the focal point position, in the case of the micro object detection apparatus 11 according to the first embodiment. The waveform $F_3$ of the detection signal $S_1$ in the case of the micro object detection apparatus 11 is indicated by a solid line in FIG. 10. In addition, the waveform $F_2$ of the ideal detection signal is indicated by a dashed line in FIG. 10, in the same way as FIG. 9.

There are two maximum peak points $Ap_4$, $Ap_5$ for one particle R, in the waveform $F_3$ of the detection signal $S_1$ indicated by the solid line in FIG. 10. There is a minimum peak point $Ap_6$ at which the output value decreases, between the two maximum peak points $Ap_4$, $Ap_5$.

In FIG. 10, the output value at the maximum peak point $Ap_4$ is a peak value $P_4$. The output value at the maximum peak point $Ap_5$ is a peak value $P_5$. The output value at the minimum peak point $Ap_6$ is a peak value $P_6$. The difference between the peak values $P_4$, $P_5$ and the peak value $P_6$ is a value $\Delta P_2$.

The value $\Delta P_2$ of the waveform $F_3$ illustrated in FIG. 10 is smaller than the value $\Delta P_1$ of the waveform $F_1$ illustrated in FIG. 9. The value $\Delta P_1$ is the difference between the maximum peak points $Ap_1$, $Ap_2$ and the minimum peak point $Ap_3$. The value $\Delta P_2$ is the difference between the maximum peak points $Ap_4$, $Ap_5$ and the minimum peak point $Ap_6$.

Hence, a threshold value for counting the number of peaks can be set high. That is, miscounting due to noise can be reduced.

That is, the micro object detection apparatus 11 according to the first embodiment can reduce miscounting of the number of peaks due to noise, as compared with the conventional micro object detection apparatus.

In FIG. 9, the value $\Delta P_1$ is a value obtained by subtracting the peak value $P_3$ at the minimum peak point $Ap_3$ from the average value of the peak value $P_1$ at the maximum peak point $Ap_1$ and the peak value $P_2$ at the maximum peak point $Ap_2$, for example. Similarly, in FIG. 10, the value $\Delta P_2$ is a value obtained by subtracting the peak value $P_6$ at the minimum peak point $Ap_6$ from the average value of the peak value $P_4$ at the maximum peak point $Ap_4$ and the peak value $P_5$ at the maximum peak point $Ap_6$, for example.

The reflection surface of the second converging mirror 102 of the micro object detection apparatus 11 according to the first embodiment has an aspherical shape. This aspherical shape has a function for generating aberration proactively.

In usual, the reflection surface is formed in an aspherical shape to prevent the aberration of the spherical mirror. The second converging mirror 102 of the micro object detection apparatus 11 has an aspherical shape to generate the aberration. Hence, the second converging mirror 102 of the micro object detection apparatus 11 generates larger aberration than the spherical mirror that approximates the aspherical shape, for example.

A least squares method or the like is used for the approximation of the aspherical shape, for example.

Moreover, when the light collection position of the second converging mirror 102 has the aberration, the light flux diameter of the light that reaches the light reception element 6 becomes larger. Hence, it is desirable that the aberration at the light collection position of the second converging mirror 102 be within the extent that the light reaching the light reception element 6 is received by the light receiving surface. Thereby, decrease in receiving efficiency of the light reception element 6 can be prevented.

In the following, a case in which this aberration is spherical aberration will be described, for example.

Spherical aberration is aberration with which an image is not formed at an ideal focal point position when the light is not a paraxial light beam. That is, the focal point position of a light beam away from a design center axis O is different from the focal point position of a light beam (paraxial light beam) in the vicinity of the design center axis O of the second converging mirror 102. Aberration other than chromatic aberration occurring due to color difference is referred to as spherical aberration in a broad sense. Note that, in the following, the spherical aberration is used in a narrow sense.

The paraxial light beam is a light beam passing through the vicinity of the optical axis and forming a small angle with the optical axis, in an optical image formation system such as a lens or a spherical mirror. The small angle is a small angle of the level that $\sin\theta$ can be approximated to angle $\theta$ ($\sin \theta \approx \theta$).

Here, in the configuration of the micro object detection apparatus 11, a light passage hole H is provided on the design center axis O of the second converging mirror 102. As illustrated in FIG. 5, a position $G_1$ is an innermost circumferential position of the reflection surface 102a. Moreover, a position $G_2$ is an outermost circumferential position of the reflection surface 102a. In FIGS. 1, 3, 4, and 5, the center axis O is illustrated as an imaginary axis.

In the second converging mirror 102, the focal point position of the light beam reflected at the outermost circumferential position $G_2$ differs from the focal point position of the light beam reflected at the innermost circumferential position $G_1$.

This is because the second converging mirror 102 has an aspherical shape, as described above.

In order to achieve the second converging mirror 102 having the spherical aberration, the reflection surface 102a is shaped to change the curvature radius from the innermost circumferential position $G_1$ to the outermost circumferential position $G_2$. That is, the reflection surface 102a is not a shape of a spherical surface. Thereby, the reflection surface 102a can generate the spherical aberration in the reflected light.

As described above, it is desirable that the spherical aberration be equal to or larger than 0.07 λrms, with regard to the light beam of the reflected light from the design center axis O to the innermost circumferential position $G_1$.

That is, it is desirable that the spherical aberration of the reflected light that passes through the passage hole H provided in the second converging mirror 102 be equal to or larger than 0.07 λrms. The passage hole H provided in the second converging mirror 102 is a hole for the light reception element 6. Part of the light that passes through this hole reaches the light reception element 6. Note that the hole for the light reception element 6 is sufficient if it can allow the scattered light L to pass therethrough. Hence, the hole for the light reception element 6 can be plugged by using a material that allows the scattered light L to pass through, for example.

Moreover, in the above description, the aberration generated by the second converging mirror 102 is spherical aberration. However, it is not a limited to this. The aberration of the reflection surface 102a may be astigmatism or coma aberration having a magnitude exhibiting the same effect. Moreover, the aberration of the reflection surface 102a may be aberration obtained by combining at least two of the spherical aberration, the astigmatism, or the coma aberration.

Note that the spherical aberration in a broad sense includes the astigmatism, the coma aberration, and the like. Hence, it is understood that the aberration of the reflection surface 102a is spherical aberration in a broad sense.

However, when the aberration of the reflection surface 102a is the spherical aberration, the distortion of the detection signal $S_1$ due to the influence of the aberration can be reduced, as compared with other aberration. This is because the spherical aberration is the most symmetric to the design center axis O. That is, the distribution of the light amount becomes symmetric on the light receiving surface of the light reception element 6.

As described above, in the micro object detection apparatus 11, the light beam 113b generated at the particle R and reflected by the second converging mirror 102 does not return to the position of the particle R, because of the spherical aberration generated on the second converging mirror 102.

The focal point of the light beam 113b is dispersed in the y axis direction, and thus it is possible to reduce blocking by the particle R itself which conventionally occurred. This makes it possible to efficiently direct the scattered light traveling the third path to the light receiving surface of the light reception element 6.

Figure 11:
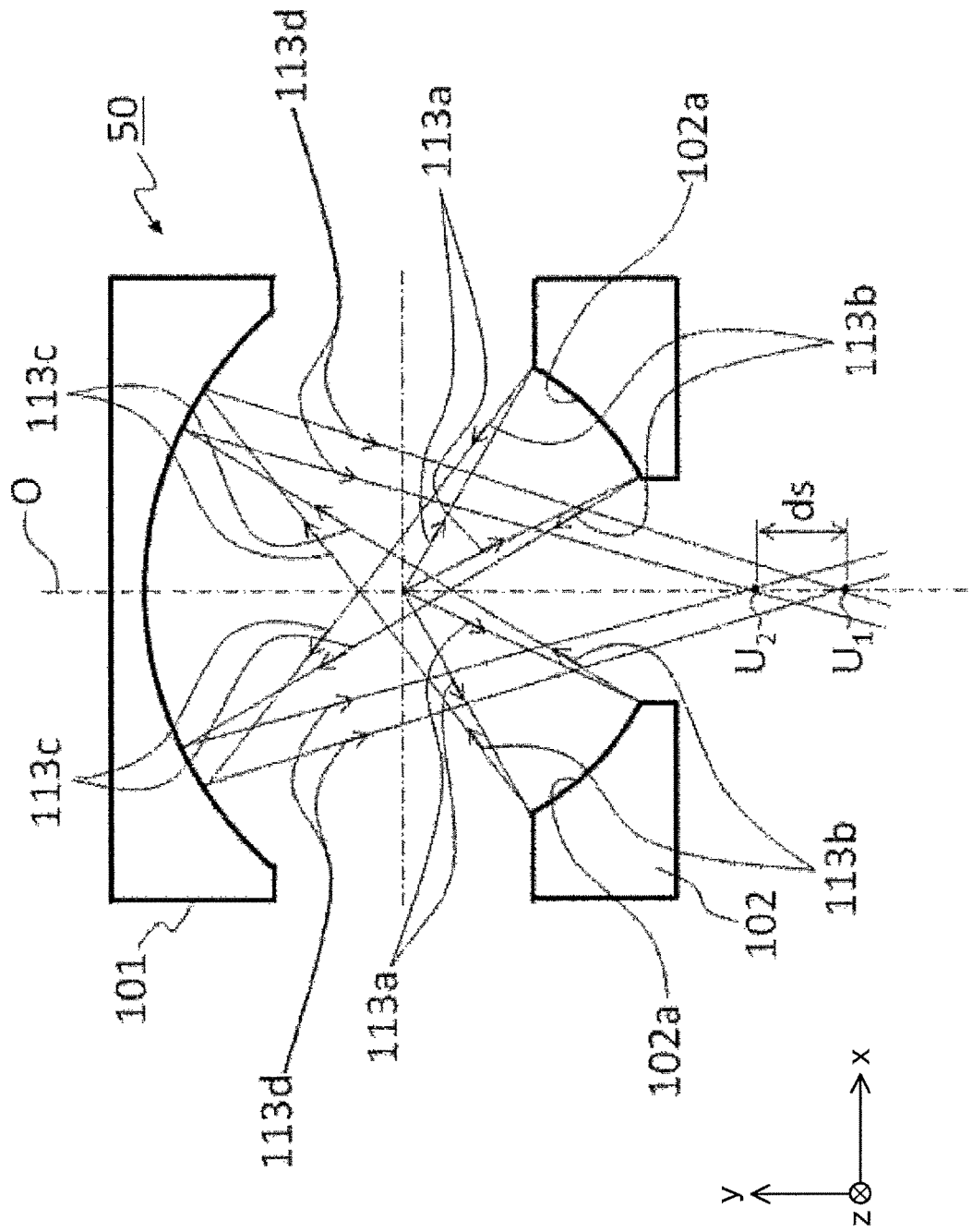
FIG. 11 is a diagram schematically illustrating a light beam on the third path in the micro object detection apparatus according to the first embodiment of the present invention.
Figure 12:
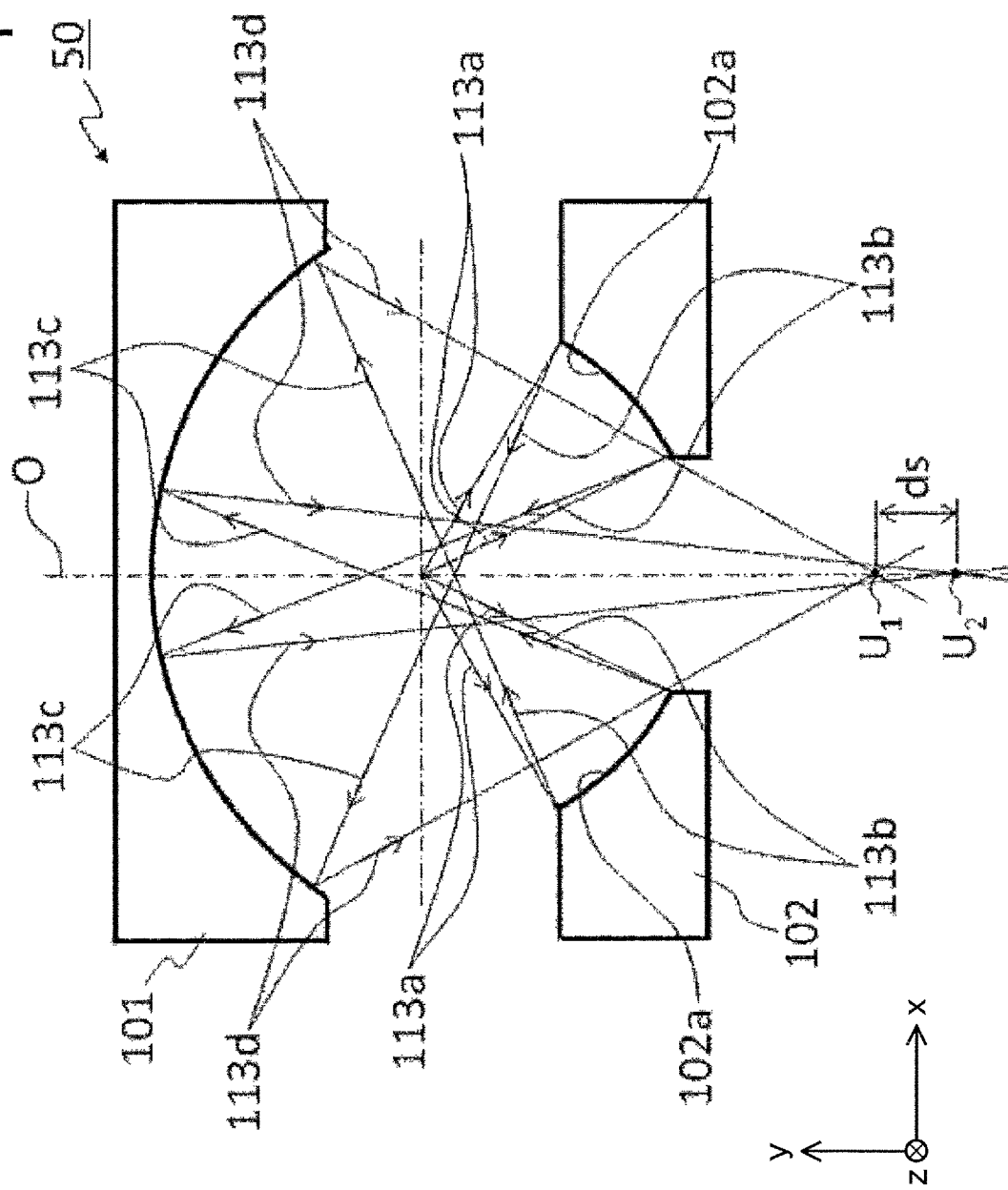
FIG. 12 is a diagram schematically illustrating a light beam on the third path in the micro object detection apparatus according to the first embodiment of the present invention.
Figure 13:
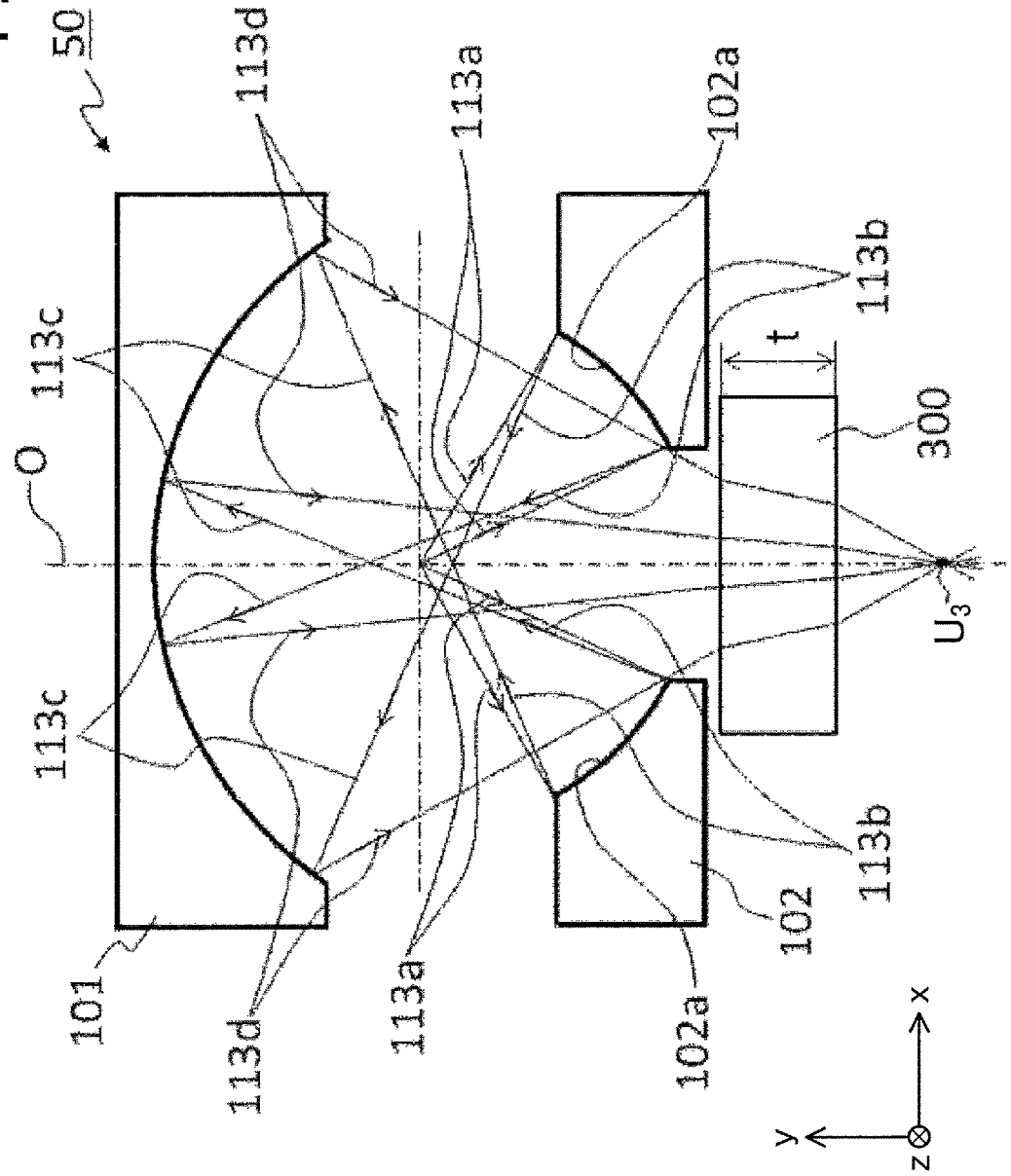
FIG. 13 is a diagram schematically illustrating a light beam on the third path in the micro object detection apparatus according to the first embodiment of the present invention.

FIGS. 11, 12, and 13 are diagrams schematically illustrating the light beam on the third path in the micro object detection apparatus 11.

The spherical aberration added to the second converging mirror 102 of the micro object detection apparatus 11 of the first embodiment will be described by using FIGS. 11, 12, and 13. For example, design matters to be considered for adding the spherical aberration to the second converging mirror 102 will be described by using FIGS. 11, 12, and 13.

FIGS. 11, 12, and 13 are diagrams in which the components other than the first converging mirror 101 and the second converging mirror 102 are omitted, in order to simplify the explanation.

In FIGS. 11 and 12, the focal point position of an off-axis light beam is represented as a focal point position $U_1$, the focal point position of a paraxial light beam is represented as a focal point position $U_2$, and the distance between the focal point position $U_1$ and the focal point position $U_2$ is represented as a distance ds.

In general, when a mirror surface is a spherical surface, the focal length at the center portion of the mirror is longer than at the peripheral portion of the mirror. Hence, spherical aberration occurs. Such spherical aberration that occurs at the spherical-shaped mirror surface at an early stage is referred to as "initial spherical aberration". With the spherical aberration, the focal point position $U_1$ of the off-axis light beam and the focal point position $U_2$ of the paraxial light beam are different in the optical axis direction.

Here, the optical axis is parallel to the y axis. The optical axis is identical with the design center axis O of the second converging mirror 102.

when additional spherical aberration is added to the initial spherical aberration, the distance ds between the focal point position $U_1$ of the off-axis light beam and the focal point position $U_2$ of the paraxial light beam further changes in the direction of the optical axis. In the following, the spherical aberration further added to the initial spherical aberration will be referred to as "additional spherical aberration". Note that, here, the initial spherical aberration is considered to be a very small value, and thus the "additional spherical aberration" is equivalent to the value of spherical aberration generated ultimately.

For example, the additional spherical aberration has polarity. This polarity includes the following two types, when it is seen in a light propagation direction along the optical axis of the optical system. First, the focal point position $U_1$ of the off-axis light beam is farther than the focal point position $U_2$ of the paraxial light beam. Second, the focal point position $U_1$ of the off-axis light beam is closer than the focal point position $U_2$ of the paraxial light beam.

Here, the distance to the focal point position $U_1$ or the distance to the focal point position $U_2$ is the distance from the position of the focal point of the second converging mirror 102, for example. Alternatively, the distance to the focal point position $U_1$ or the distance to the focal point position $U_2$ is the distance from the position of the first focal point of the first converging mirror 101, for example.

FIG. 11 is a diagram illustrating an example of the first case. FIG. 12 is a diagram illustrating an example of the second case.

The polarity of the change of the distance ds from the initial spherical aberration may be any one of the cases illustrated in FIGS. 11 and 12. The change of the distance ds from the initial spherical aberration is generated by the additional spherical aberration of the second converging mirror 102 of the micro object detection apparatus 11 illustrated in the first embodiment.

In the following, the size to which the additional spherical aberration is set in designing the micro object detection apparatus 11 illustrated in the first embodiment will be described.

Here, the polarity of the additional spherical aberration illustrated in FIG. 12 will be described as an example.

FIG. 13 is a diagram of the configuration illustrated in FIG. 12 that additionally includes a parallel flat plate 300 inserted in the course of the light beam 113*d* as a simulation.

In general, when a parallel flat plate of a certain thickness is inserted in the course of the collected light, the focal point position $U_1$ of the off-axis light beam moves in a direction in which it approaches the focal point position $U_2$ of the paraxial light beam, in the light propagation direction along the optical axis of the optical system. This action corrects the additional spherical aberration, and the parallel flat plate 300 can move the focal point position $U_1$ and the focal point position $U_2$ to the same focal point position $U_3$.

For example, the numerical aperture NA of the light beam group of the light beam 113*d* is set to 0.4226 (the light flux divergence angle of approximately 25°); the light wavelength is set to 660 nm; the refractive index n of the parallel flat plate 300 is set to 1.5; and the thickness of the parallel flat plate 300 is set to thickness t. Here, the "light beam group" is a light flux.

For example, the particle size of dust or pollen is assumed to be from 20 μm to 100 μm. In this case, it is desirable that the additional spherical aberration be from 6 λpv to 30 λpv. The additional spherical aberration can be increased up to 50 λpv. That is, an effect of detecting the dust or the pollen can be expected by setting the additional spherical aberration from 6 λpv to 50 λpv.

As described above, in general, the spherical aberration of the light in a collected state is smaller than 0.07 λrms. The PV value of the spherical aberration is obtained by multiplying the RMS value of the aberration by a coefficient $6\sqrt{5}$ ($\approx 13.41641$). Thus, 0.07 λrms is approximately 0.939 λpv. 6 λpv is approximately 6.4 times the value corresponding to 0.07 λrms. Moreover, 30 λpv is approximately 32 times the value corresponding to 0.07 λrms. Moreover, 50 λpv is approximately 53.2 times the value corresponding to 0.07 λrms.

A case in which the additional spherical aberration is set to 30 λpv will be described. The relationship between the thickness t, the refractive index n, the NA for the light flux and the spherical aberration W40 pv of the parallel flat plate 300 is expressed by the following equation 1.

$$W40\ pv = (t/8) \times ((n^2-1)/n^3) \times NA^4 \quad (1)$$

The additional spherical aberration of the second converging mirror 102 is set to 30 λpv when the parallel flat plate 300 is not used. The light wavelength is set to 660 nm; the NA is set to 0.4226; and the refractive index n is set to 1.5. If the parallel flat plate 300 is added under this condition, the thickness d of 13.4 mm is necessary for the parallel flat plate 300 in order to correct the additional spherical aberration (30 λpv) of the second converging mirror 102 to zero.

As described above, the second converging mirror 102 is designed by expediently assuming the parallel flat plate 300 illustrated in FIG. 13, for example. The parallel flat plate 300 is a means for generating the spherical aberration.

That is, at the time of designing, the second converging mirror 102 is designed so as to make the distance ds to be zero when the parallel flat plate 300 is disposed. That is, the reflection surface of the second converging mirror 102 is formed to be an aspherical surface. The thickness d of the parallel flat plate 300 is changed, according to the value of the spherical aberration to be set.

Thereby, the spherical aberration of the second converging mirror 102 can be set in the above range of 6 λpv to 50 λpv. Thus, the light beam 113*b* generated at the particle R and reflected by the second converging mirror 102 does not converge at the position of the particle R again.

Conversely, the magnitude of the spherical aberration of the second converging mirror 102 can be checked by using the parallel flat plate 300. That is, by preparing several parallel flat plates 300 of different thicknesses t, it is checked which one of the parallel flat plates 300 makes the aberration small.

The blocking the scattered light by the particle R itself, which conventionally occurred, can be reduced by dispersing the focal points of the light beam 113*b* in the y axis direction (the optical axis direction of the second converging mirror 102). Thereby, the scattered light on the third path can be directed to the light receiving surface of the light reception element 6 efficiently.

As described in the above example, the spherical aberration is smaller than 0.07 λrms, in a state that light is collected. In consideration of this, the additional spherical aberration (6 λpv to 50 λpv) generated at the second converging mirror 102 is not within the extent that is generated due to a production error occurring when the second converging mirror 102 is simply processed to have a spherical surface. The design is made by taking proactively generating the spherical aberration into consideration.

In the above description, particles of dust or pollen which are comparatively large in diameter are assumed, when the aspherical shape of the second converging mirror 102 is designed. However, the micro object detection apparatus 11 has a purpose to detect a small particle, in some cases. The small particle has a particle diameter of 10 μm (PM10), 2.5 μm (PM2.5), or the like, for example.

In a case of detection of a small particle (for example, PM10 or PM2.5), the air actually contains pollen or dust larger than the small particle. Hence, the large particles cause erroneous detection at the time of detection of the small particle (for example, PM10 or PM2.5) as a detection target. However, the small particle is not limited to PM10 or PM2.5. It can be another particle, such as PM1 or PM0.5.

That is, the intensity of the scattered light from the large particle is reduced due to blocking by the large particle itself. The scattered light of which the light intensity is reduced is incident on the light reception element 6. When the intensity of the scattered light from the large particle is approximately equal to the intensity of the scattered light from the small particle (PM10 or PM2.5), the light blocking of the scattered light by the large particle itself causes erroneous detection.

Thus, even in the case of the micro object detection apparatus 11 for detecting a small particle (PM10 or PM2.5), it is necessary to consider the shape of the aspherical surface of the second converging mirror 102, assuming that there are large particles, in order to prevent the erroneous detection. The large particle is a particle of dust or pollen having a diameter of 20 μm to 100 μm, or the like, for example.

In the micro object detection apparatus 11 according to the first embodiment, which is described above, the light beam 113*b* generated at the particle R and reflected by the second converging mirror 102 does not converge at the position of the particle R again. Thus, light blocking of the light beam 113*b* by the particle R itself, which conventionally occurred, can be reduced. In addition, the shielding by the particle R itself, which conventionally occurred, can be reduced effectively. Thereby, the scattered light (the light beam 113a) on the third path can be directed to the light receiving surface of the light reception element 6 efficiently Moreover, the micro object detection apparatus 11 can prevent generation of a quasi peak like the maximum peak points $Ap_1$, $Ap_2$ in FIG. 9. Thus, miscounting (miscounting) of the number of particles R in the peak number counter 63 can be reduced. Thus, the accuracy of measuring the number of particles R, the number of particles R per unit volume, the weight of the particles R per unit volume, and the like can be improved.

The configuration of the first embodiment can also be applied to the configurations of other second and third embodiments described later.

Second Embodiment

Figure 14:
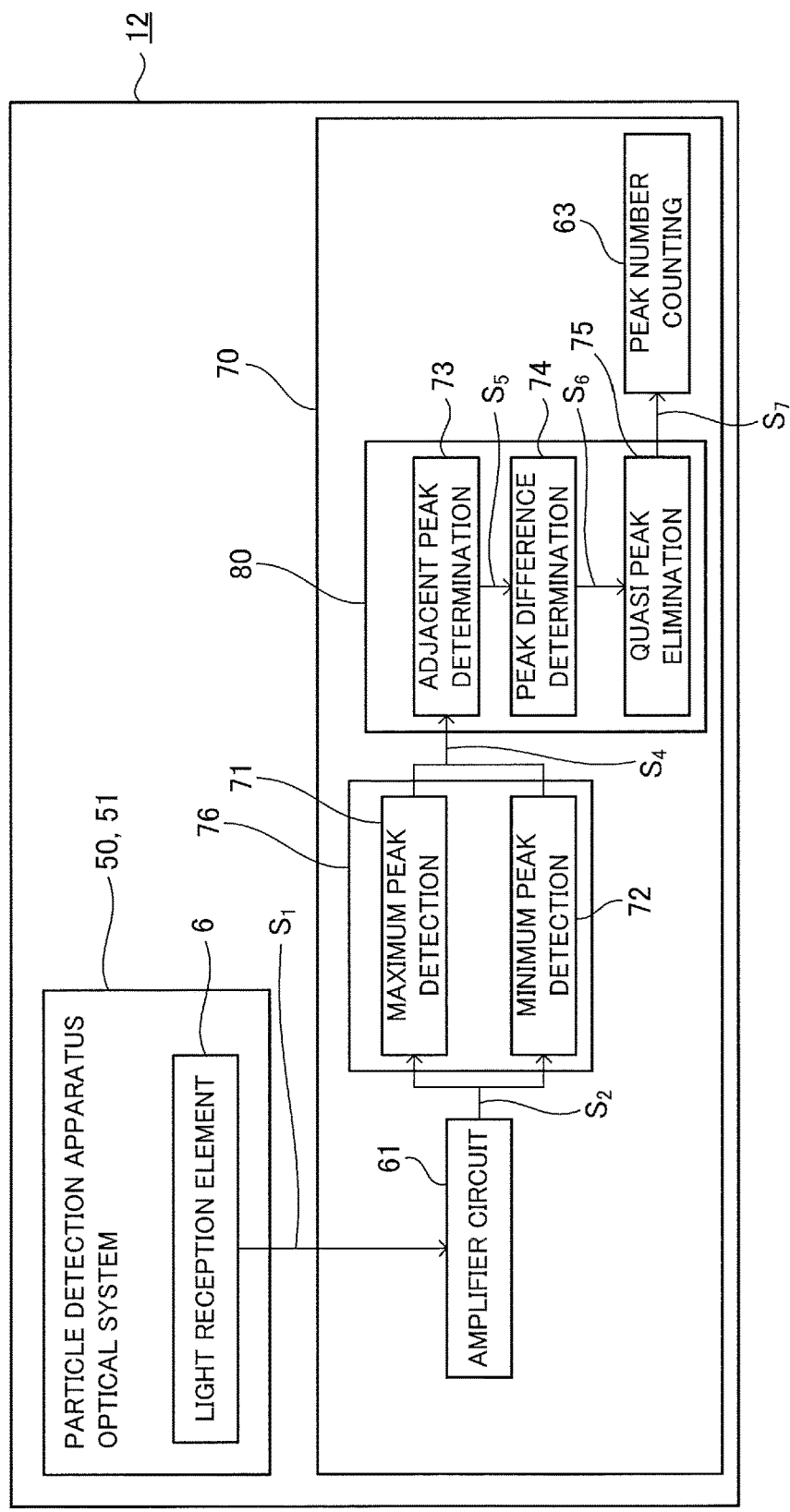
FIG. 14 is a block diagram illustrating a detection circuit unit of a micro object detection apparatus according to a second embodiment of the present invention.

FIG. 14 is a block diagram illustrating a detection circuit unit 70 of a micro object detection apparatus 12 according to a second embodiment.

The micro object detection apparatus 12 differs from the micro object detection apparatus 11 according to the first embodiment only with regard to a part corresponding to the detection circuit unit 60. That is, the micro object detection apparatus 12 can include the detection optical system 50 of the micro object detection apparatus 11. In addition, the micro object detection apparatus 12 can include the detection optical system 51 of the conventional micro object detection apparatus.

Thus, detailed description will be omitted, with regard to the configuration of the detection optical system of the micro object detection apparatus 12.

With the configuration of the detection optical system 51, the micro object detection apparatus 12 exerts its effect, when the waveform $F_1$ of the detection signal $S_1$ for one particle R includes two maximum peak points $Ap_1$, $Ap_2$ and one minimum peak point $Ap_3$. That is, the micro object detection apparatus 12 exerts its effect when the detection signal $S_1$ is the waveform $F_1$ illustrated in FIG. 9 described in the first embodiment.

Moreover, with the configuration of the detection optical system 50, the micro object detection apparatus 12 exerts its effect, when two maximum peaks $Ap_4$, $Ap_5$ remain in the waveform $F_3$ illustrated in FIG. 10. In addition, the micro object detection apparatus 12 exerts its effect, when the detection signal $S_1$ includes a quasi peak.

In the following, the configuration of the detection circuit unit 70 of the micro object detection apparatus 12 according to the second embodiment will be described by using the block diagram of FIG. 14.

The detection circuit unit 70 includes a maximum peak detector 71, a minimum peak detector 72, and a particle determination unit 80. A peak detector 76 includes the maximum peak detector 71 and the minimum peak detector 72. Moreover, the detection circuit unit 70 can include an amplifier circuit 61 and a peak number counter 63. The particle determination unit 80 includes an adjacent peak determination unit 73. The particle determination unit 80 can include a peak difference determination unit 74 or a quasi peak elimination unit 75.

The following description will be given by using the reference signs of FIG. 9, for example.

The amplifier circuit 61 amplifies or attenuates the level of an output signal $S_1$. The amplifier circuit 61 outputs a signal $S_2$.

The signal $S_2$ is obtained by amplifying or attenuating the level of the output signal $S_1$.

The amplifier circuit 61 can be removed when a sufficient signal level is satisfied in the subsequent processing, for example.

The peak detector 76 receives the signal $S_2$. The maximum peak detector 71 detects the maximum peak points $Ap_1$, $Ap_2$ of the output signal $S_2$ of the amplifier circuit 61. The maximum peak detector 71 sequentially processes the detection of the maximum peak points $Ap_1$, $Ap_2$ of the output signal $S_2$. The minimum peak detector 72 detects the minimum peak point $Ap_3$ of the output signal $S_2$ of the amplifier circuit 61. The minimum peak detector 72 sequentially processes the detection of the minimum peak point $Ap_3$ of the output signal $S_2$. The peak detector 76 outputs a signal $S_4$.

The particle determination unit 80 receives the signal $S_4$. The signal $S_4$ includes information on the maximum peak points $Ap_1$, $Ap_2$ output by the maximum peak detector 71 and information on the minimum peak point $Ap_3$ output by the minimum peak detector 72. The particle determination unit 80 determines whether or not the maximum peaks are maximum peaks generated in a quasi manner.

The particle determination unit 80 includes the adjacent peak determination unit 73. The particle determination unit 80 can include the peak difference determination unit 74 or the quasi peak elimination unit 75.

The adjacent peak determination unit 73 receives the signal $S_4$. The adjacent peak determination unit 73 determines whether or not each of the peak value $P_1$ and the peak value $P_2$ is a value of a maximum peak point Ap that is adjacent temporally. The detection results (signal $S_4$) of the maximum peak detector 71 and the minimum peak detector 72 are used in the determination of the adjacent peak determination unit 73. That is, the peak values $P_1$, $P_2$ detected by the maximum peak detector 71 and the peak value $P_3$ detected by the minimum peak detector 72 are used in the determination for the adjacent peak determination unit 73.

The adjacent peak determination unit 73 determines whether or not the peak value $P_1$ and the peak value $P_2$ are the quasi peaks of the maximum peak point Ap.

The adjacent peak determination unit 73 determines whether or not the maximum peak value $P_1$, the maximum peak value $P_2$, and the minimum peak value $P_3$ are detected in the order of the maximum peak value $P_1$, the minimum peak value $P_3$, and the maximum peak value $P_2$. The adjacent peak determination unit 73 sends the determination result (signal $S_5$) of whether or not the peak values $P_1$, $P_2$, $P_3$ are in this order ($P_1 \rightarrow P_3 \rightarrow P_2$), to the peak difference determination unit 74 of the subsequent stage. The adjacent peak determination unit 73 outputs the signal $S_5$.

The adjacent peak determination unit 73 determines whether or not the minimum peak value $P_3$ is between the maximum peak value $P_1$ and the maximum peak value 92.

The peak difference determination unit 74 receives the signal $S_5$. The peak difference determination unit 74 determines the magnitude relationship between the absolute difference value $\Delta P_1$ and a set difference value $\Delta P_0$, on the basis of the result of the determination (signal $S_5$) by the adjacent peak determination unit 73.

The peak difference determination unit 74 determines whether or not the absolute difference value $\Delta P_1$ between the peak value $P_1$ and the peak value $P_3$ is larger than a preset set difference value $\Delta P_0$, for example. The absolute difference value $\Delta P_1$ is the absolute value of the value obtained by subtracting the peak value $P_3$ from the average value of the peak value $P_1$ and the peak value $P_2$, for example.

When the absolute difference value $\Delta P_1$ is larger than the preset difference value $\Delta P_0$, the peak difference determination unit 74 determines that a particle R existed at each of the maximum peak point $Ap_1$ and the maximum peak point $Ap_2$.

The value of the maximum peak point $Ap_1$ is the maximum peak value $P_1$. The value of the maximum peak point $Ap_2$ is the maximum peak value $P_2$. Thus, the peak number counter 63 adds "2" to the count number, assuming that two particles R existed.

On the other hand, when the absolute difference value $\Delta P_1$ is smaller than the preset difference value $\Delta P_0$, the peak difference determination unit 74 determines that a quasi maximum peak was generated in the detection signal $S_1$. The quasi maximum peak is generated by the shielding effect of the particle R itself. The peak difference determination unit 74 determines that one particle R existed, from the combination of the maximum peak point $Ap_1$ and the maximum peak point $Ap_2$. Thus, the peak number counter 63 adds "1" to the count number, assuming that one particle R existed.

Note that the quasi maximum peak has the same meaning as the above quasi peak.

Moreover, the peak difference determination unit 74 can determine the maximum peak values $P_1$, $P_2$ and the minimum peak value $P_3$, by using a value other than the absolute difference value $\Delta P_1$. For example, the peak difference determination unit 74 can determine the maximum peak values $P_1$, $P_2$ and the minimum peak value $P_3$ by using a ratio of the maximum peak values $P_1$, $P_2$ and the minimum peak value $P_3$. That is, the peak difference determination unit 74 can use the difference, the ratio, or the like between the maximum peak values $P_1$, $P_2$ and the minimum peak value $P_3$.

The peak difference determination unit 74 outputs a signal $S_6$.

The quasi peak elimination unit 75 receives the signal $S_6$. The quasi peak elimination unit 75 determines whether or not to eliminate the quasi maximum peak, on the basis of the determination result (signal $S_6$) by the peak difference determination unit 74. The quasi maximum peak is a peak of the detection signal $S_1$ generated by the shielding effect of the particle R itself.

The quasi peak elimination unit 75 outputs a signal $S_7$.

The peak number counter 63 counts the number of peaks corresponding to the detection of the particle R, on the basis of the determination result (signal $S_7$) of the particle determination unit 80.

The number concentration or the weight concentration of the particles R can be calculated by using the count value of the number of peaks obtained by the peak number counter 63 of the detection circuit 60 or the detection circuit 70.

The micro object detection apparatuses 11, 12 calculate the number concentration or the weight concentration of the particles R, by using the count value of the number of peaks.

For example, the number concentration of the particles R is calculated by dividing the count value during a predetermined certain amount of time, by a gas volume, a liquid volume, or the like.

According to the micro object detection apparatus 12 of the second embodiment, which has been described above, the error in counting (miscounting) the number of particles R in the detection circuit unit 70 due to the generation of the quasi peak can be reduced. In addition, the measurement accuracy of the number concentration, the weight concentration, or the like can be improved.

Third Embodiment

Figure 15:
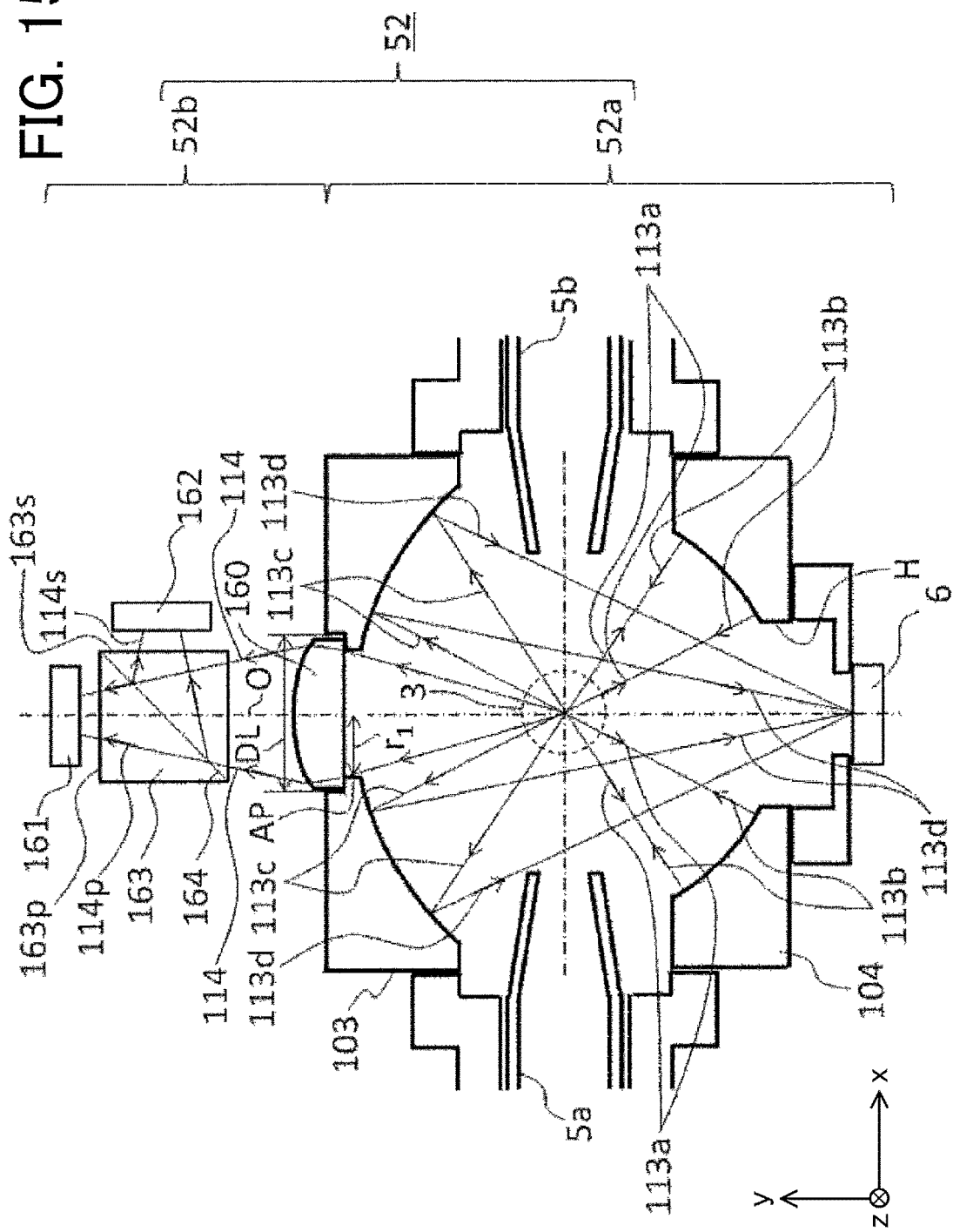
FIG. 15 is a configuration diagram schematically illustrating a configuration of a detection optical system of a micro object detection apparatus according to a third embodiment of the present invention.

FIG. 15 is a configuration diagram schematically illustrating a configuration of a detection optical system 52 of the micro object detection apparatus 11 according to a third embodiment.

The detection optical system 52 of the micro object detection apparatus 11 according to the third embodiment includes another detection optical system (second detection optical system 52b), in the conventional detection optical system 51 illustrated in FIG. 8, the detection optical system 50 of the first embodiment, and the detection optical system 50 of the second embodiment. In the following, the detection optical systems 50, 51 are referred to as a first detection optical system. In the third embodiment, the part corresponding to the detection optical systems 50, 51 is referred to as a first detection optical system 52a.

The second detection optical system 52b mainly receives the scattered light (a light beam 114 on a fourth path) that directly passes through an opening AP, among the scattered light emitted from the particle R. Then, the second detection optical system 52b detects the optical property of the particle R, on the basis of the light beam 114. The opening AP is provided in the first converging mirror 103.

For example, the second detection optical system 52b detects the size or the shape of the particle R, for example. In addition, the second detection optical system 52b identifies the type of the particle R from the fluorescence property or the like of the particle R, for example. That is, the second detection optical system 52b is a detection optical system that can classify the features of the particles R.

With the second detection optical system 52b, the micro object detection apparatus 11 can determine a larger number of types of particles R than in the past. Moreover, the micro object detection apparatus 11 can determine the particle R more accurately than in the past.

In the third embodiment, the second detection optical system 52b can detect the property of the particle R or the like, without impairing the efficiency of the scattered light of the light beam 113d. The scattered light of the light beam 113d is the scattered light directed to the light reception element 6 via the first converging mirror 103 and the second converging mirror 104.

In the following, the second detection optical system 52b detects polarized light components of the scattered light of the particle R, for example. The second detection optical system 52b determines the type of the particle R on the basis of the information indicating the shape of the particle R which is obtained from the polarized light components of the scattered light. The second detection optical system 52b determines the particle of the pollen and the particle of the dust (dust), for example. The particle of the pollen has a shape close to a spherical shape. On the other hand, the particle of the dust has an aspherical shape.

Figure 16:
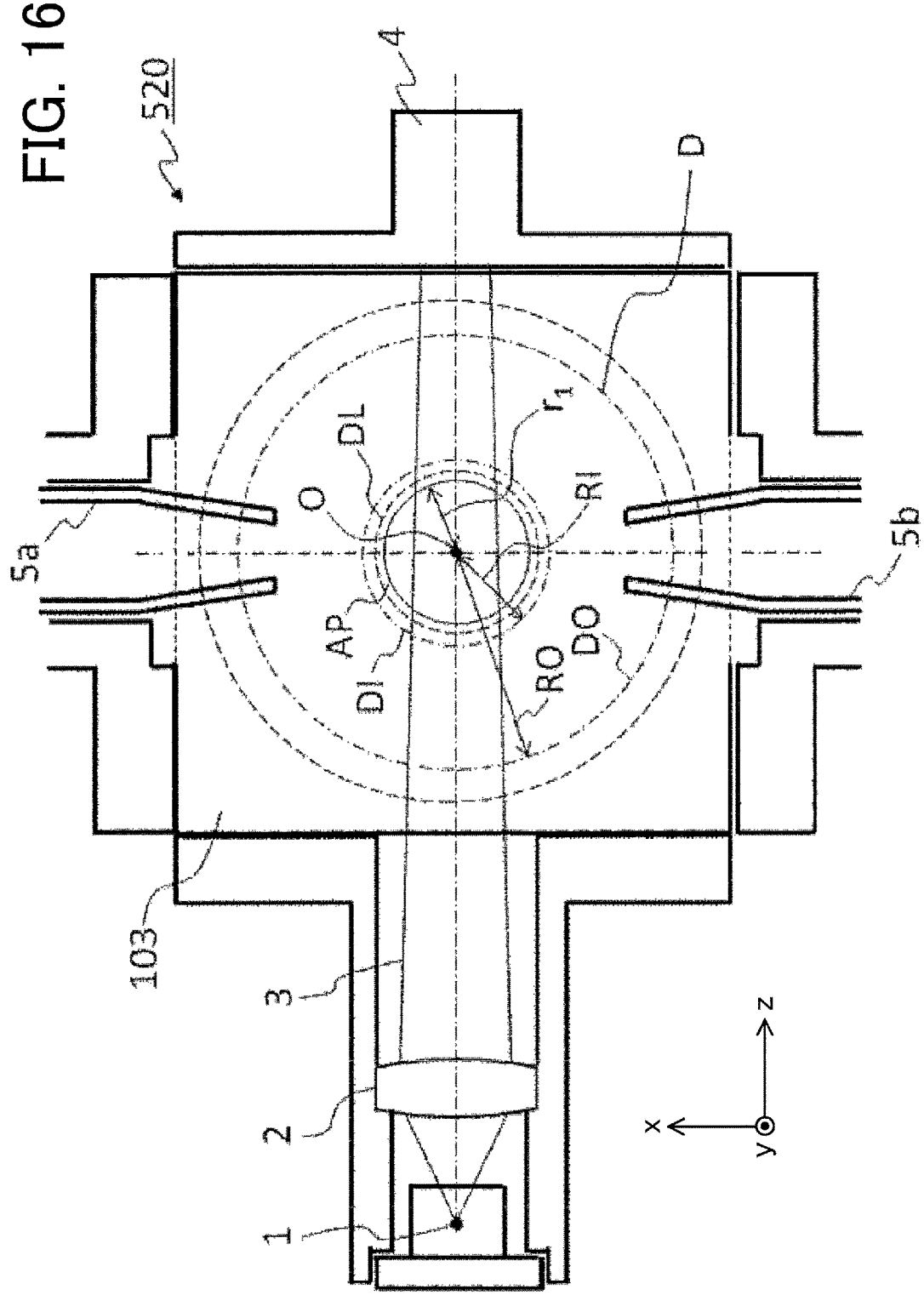
FIG. 16 is a configuration diagram schematically illustrating a configuration of an optical system of the micro object detection apparatus according to the third embodiment of the present invention.

FIGS. 15 and 16 are configuration diagrams schematically illustrating the configuration of the optical system 52 of the micro object detection apparatus 11 according to the third embodiment, for example.

FIG. 15 is a configuration diagram illustrating a cross section in the x-y plane of the detection optical system 52 of the micro object detection apparatus 11. In FIG. 15, the second detection optical system 52b includes a lens 160, light reception elements 161, 162, and a polarization prism 163. However, a member that holds these components is omitted.

FIG. 16 is a configuration diagram illustrating a cross section in the z-x plane of the optical system 520 of the micro object detection apparatus 11. However, to make the description easy, the lens 160, the polarization prism 163, the light reception element 161, and the light reception element 162 of the second detection optical system 52b are omitted in FIG. 16.

The detection optical system 52 includes the second detection optical system 52b in addition to the detection optical system 50.

In the detection optical system 52, the second detection optical system 52b is provided on the first converging mirror 103 side. The first converging mirror 103 faces the second converging mirror 104.

The opening AP is an opening to take the scattered light (the light beam 114) from the particle R into the second detection optical system 52b. The opening AP is provided in the first converging mirror 103.

The opening AP is located on the center axis O of the first converging mirror 103, for example. In FIGS. 15 and 16, the center of the opening AP is located on the center axis O.

As illustrated in FIG. 16, the opening AP has a circle shape. The radius of the opening AP is radius $r_1$. However, the shape is not limited to this, but may be other than the circle.

The scattered light 113b reflected by the second converging mirror 104 is directed to the light reception element 6 via the first converging mirror 103. In the third embodiment, the opening AP is formed in the first converging mirror 103, such that the scattered light 113b does not reach the opening AP, for example. The opening AP is positioned inside the region surrounded by the points at which the scattered light 113b reflected by the periphery of the passage hole H reaches the first converging mirror 103. That is, the opening AP is located inside the shape of the periphery of the passage hole H projected on the first converging mirror 103 by the scattered light 113b.

Moreover, the opening AP can include the region surrounded by the points at which the scattered light 113b reflected by the periphery of the passage hole H reaches the first converging mirror 103. That is, the opening AP can include the region surrounded by the shape of the periphery of the passage hole H projected on the first converging mirror 103 by the scattered light 113b.

A hole DL is a hole for installing the lens 160, for example.

The hole DL is provided in the first converging mirror 103.

The hole DL is located on the same axis as the opening AP, for example. The end portion of the −y axis side of the hole DL is connected to the end portion of the +y axis side of the opening AP. For example, the diameter of the hole DL is larger than the diameter of the opening AP.

The lens 160 is inserted in the hole DL, from the +y axis side of the hole DL. The diameter of the lens 160 is larger than the diameter of the hole DL. The position of the lens 160 in the y axis direction in relation to the first converging mirror 103 is decided at the end portion of the +y axis side of the opening AP. The position of the lens 160 on the z-x plane is decided by the hole DL.

The lens 160 allows the scattered light (the light beam 114) from the particle R to directly enter thereinto. The lens 160 converges the incident scattered light (the light beam 114), for example. The lens 160 forms light spots on the light reception elements 161, 162.

The lens 160 is an example of a light converging element for converging the scattered light (the light beam 114) from the particle R. Note that the lens 160 is not needed necessarily.

The polarization prism 163 is located on the +y axis side of the lens 160.

The polarization prism 163 is an example of a polarized light separating element.

The scattered light (the light beam 114) coming from the lens 160 is separated by the polarization prism 163. The light coming from the lens 160 is separated by the polarization prism 163, on the basis of the light polarization direction of the light. For example, the P-polarized light (a light beam 114p) travels to the light reception element 161 from the polarization prism 163. The S-polarized light (a light beam 114s) travels to the light reception element 162 from the polarization prism 163.

The oscillation of the P-polarized light (the light beam 114p) is orthogonal to the oscillation of the S-polarized light (the light beam 114s). That is, the P-polarized light (the light beam 114p) oscillates orthogonally to the oscillation of the S-polarized light (the light beam 114s).

The light reception elements 161, 162 are located to face the polarization prism 163. For example, the light reception element 161 is located to face a P-polarized light (light beam 114p) projection surface 163p of the polarization prism 163. For example, the light reception element 162 is located to face an S-polarized light (light beam 114s) projection surface 163s of the polarization prism 163.

The scattered light detected by the light reception element 161 is the P-polarized light (the light beam 114p) that has transmitted through the polarization prism 163. On the other hand, the scattered light detected by the light reception element 162 is the S-polarized light (the light beam 114s) reflected by a reflection surface 164 of the polarization prism 163. The S-polarized light component is the component in the orthogonal direction to the P-polarized light component.

Here, the intensity of the light detected by the light reception element 161 is Ip, and the intensity of the light detected by the light reception element 162 is Is.

For example, the shape of the particle R can be detected, using the polarization degree expressed by the following equation 2 as an index. The "shape of the particle R" is the degree of flatness with reference to a true spherical shape, for example. This degree of flatness is referred to as "sphericity degree".

$$\text{Polarization degree (sphericity degree)} = (Ip - Is)/(Ip + Is) \quad (2)$$

The type of the particle R can be identified by computation using equation 2. However, the computation equation for calculating the sphericity degree is not limited to this. The computation equation may be another computation equation whose value changes according to the shape of the particle R similarly.

As described above, the micro object detection apparatus 11 includes the first detection optical system 52a and the second detection optical system 52b. The first detection optical system 52a collects the scattered light by using the converging mirrors 103, 104, and detects a fine particle. On the other hand, the second detection optical system 52b allows the scattered light (the light beam 114) to directly enter thereinto, and detects a fine particle.

Providing a polarized light optical system as the second detection optical system 52b is effective, when there is a need for a polarized light optical system for detecting the P-polarized light and the S-polarized light included in the scattered light, as described above. This is because, when the scattered light from the particle R is reflected, for example, by the first converging mirror 103, the second converging mirror 104, or the like, the ratio of the P-polarized light and the S-polarized light changes. Thus, an error is caused in determination of the shape (the sphericity degree) of the particle R by using the polarization degree as an index, and the accuracy of identification of the type of the particle R decreases.

Moreover, when the first detection optical system 52a detects the scattered light by using the first converging mirror 103 and the second converging mirror 104, a direction of the detection by the first detection optical system 52a covers a wide range. That is, the first detection optical system 52a receives the lateral scattered light Ls, the forward scattered light Lfs, and the backward scattered light Lbs. The detection by the first detection optical system 52a receives the lateral scattered light Ls of a wide range, for example.

However, detecting the direct scattered light from the particle R is effective, when the feature of the particle R can be detected by detecting only one of the lateral scattered light Ls, the forward scattered light Lfs, and the backward scattered light Lbs. In this case, the light received by the light reception element can be limited to the scattered light in a certain direction. In the case of such a detection target, using the second detection optical system 52b is effective.

Positions DI, DO illustrated in FIG. 16 are the positions of the scattered light (the light beam 113c) that is reflected by the second converging mirror 104 and reaches the first converging mirror 103. The positions DI indicate the positions of the closest side to the center axis O. The positions DO indicate the positions of the farthest side from the center axis O. In FIG. 16, the positions DI are represented by an alternate long and short dash line. The positions DO are represented by an alternate long and short dash line.

Here, each of the positions DI and the positions DO is a circle, to make the description easy. The radius of the positions DI is a radius RI. The radius of the positions DO is a radius RO.

That is, the light beam 113c of the scattered light reaches between the positions DI and the positions DO on the first converging mirror 103.

The passage hole H for taking the scattered light is provided on the second converging mirror 104 side, in the micro object detection apparatus 11 that detects the scattered light by the two opposite converging mirrors 103, 104. The scattered light accepted through this passage hole H is received by the light reception element 6.

In the case of such an optical system, there is a region that the light beam 113c reflected by the second converging mirror 104 does not reach, near the center axis O on the first converging mirror 103. The region that the light beam 113c does not reach is the inside of the positions DI.

The opening AP is provided in the region on this first converging mirror 103 which the light beam 113c does not reach.

Thereby, the scattered light (the light beam 114) that directly reaches from the particle R can be accepted through the opening AP. In addition, the efficiency of the scattered light (the light beam 113c) directed to the light reception element 6 via the first converging mirror 103 and the second converging mirror 104 is not impaired. The first detection optical system 52a can efficiently direct the light beam 113c of the scattered light to the light reception element 6.

Here, the center of the opening AP may be offset from the center axis O, within a range having a small influence on the reflection efficiency of the scattered light on the first converging mirror 103. Moreover, the radius $r_1$ of the opening AP may be large to allow the light beam 113c of the scattered light to enter into the opening AP.

Moreover, when influence on the accuracy of detection in the second detection optical system 52b is small, the center of the opening AP may be moved from the center axis O. That is, the opening AP can be located on the reflection surface of the first converging mirror 103.

In FIG. 16, the radius $r_1$ is set smaller than the radius RI. If the opening AP is set to satisfy this condition, the efficiency of the scattered light directed to the light reception element 6 via the first converging mirror 103 and the second converging mirror 104 is not impaired. Thus, the first detection optical system 52a can efficiently direct the light beam 113c of the scattered light to the light reception element 6.

The detection optical system 52 of FIGS. 15 and 16 includes the lens 160. However, when the detection efficiency of the scattered light is sufficient, the lens 160 can be removed as necessary. In that case, the hole DL provided in the first converging mirror 103 is unnecessary. That is, the penetrating opening AP is provided in the first converging mirror 103.

Moreover, the first converging mirror 103 can have a function of the lens 160, as another form of the micro object detection apparatus 11 according to the third embodiment. That is, in the third embodiment, the lens 160 is integrated with the first converging mirror 103. A region (a lens portion 165) provided on the first converging mirror 103 and having a lens function allows the light to transmit toward a second detection optical system 53b side.

Figure 17:
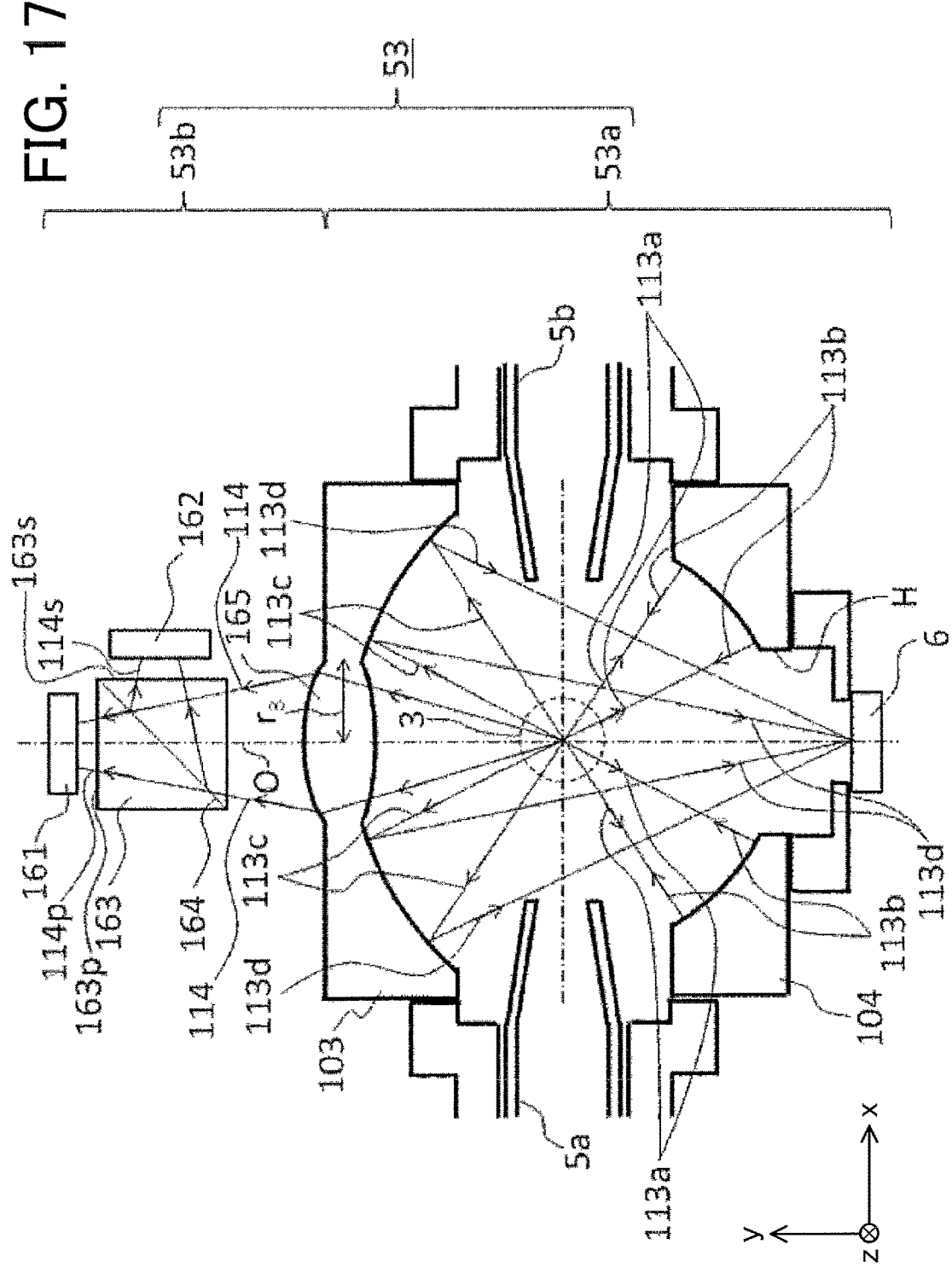
FIG. 17 is a configuration diagram schematically illustrating a configuration of an optical system of the micro object detection apparatus according to the third embodiment of the present invention.

FIG. 17 is a configuration diagram schematically illustrating a configuration of a detection optical system 53 of another form of the micro object detection apparatus 11 according to the third embodiment of the present invention.

The detection optical system 53 includes a first detection optical system 53a and a second detection optical system 53b.

A lens portion 165 is provided in the first converging mirror 103. The lens portion 165 is located on the center axis O of the first converging mirror 103, for example.

The lens portion 165 can direct the scattered light (the light beam 114) from the particle R to the second detection optical system 53b. In FIG. 17, the radius of the lens portion 165 is a radius $r_3$. In FIG. 17, the lens portion 165 converges the incident scattered light. The scattered light converged by the lens portion 165 is incident on the polarization prism 163.

FIG. 18 is a block diagram illustrating a detection circuit unit 65 of a micro object detection apparatus 13 that includes the detection optical system 53. Note that the micro object detection apparatus 13 illustrated in FIG. 18 can include the detection optical system 52.

The detection circuit unit 65 includes maximum peak detectors 62a, 62b, 62c, a peak number counter 63, and a particle type determination unit 64. The detection circuit unit 65 can include amplifier circuits 61a, 61b, 61c or a maximum peak detector 62a.

The light reception elements 6, 161, 162 output signals $S_{11}$, $S_{12}$, $S_{13}$, similarly to the detection circuit unit 60 of FIG. 7.

The amplifier circuits 61a, 61b, 61c receive the signals $S_{11}$, $S_{12}$, $S_{13}$. The amplifier circuits 61a, 61b, 61c amplify or attenuate the signals $S_{11}$, $S_{12}$, $S_{13}$. The amplifier circuits 61a, 61b, 61c output signals $S_{21}$, $S_{22}$, $S_{23}$. The amplifier circuits 61a, 61b, 61c can be removed, if the sufficient signal level is satisfied in the subsequent processing, for example.

The maximum peak detectors 62a, 62b, 62c receive the signals $S_{21}$, $S_{22}$, $S_{23}$. The maximum peak detectors 62a, 62b, 62c detect the maximum peak points of the output signals $S_{21}$, $S_{22}$, $S_{23}$ of the amplifier circuits 61a, 61b, 61c. The maximum peak points of the output signals $S_{21}$, $S_{22}$, $S_{23}$ correspond to the particle R. The maximum peak detectors 62a, 62b, 62c sequentially process the detection of the maximum peak points of the output signals $S_{21}$, $S_{22}$, $S_{23}$. Note that the maximum peak detector 62a can be removed, if the number of particles R can be counted by using a threshold value or the like, without detecting the maximum peak point, for example.

The peak number counter 63 receives signals $S_{31}, S_{32}, S_{33}$ indicating the maximum peak points, which are output by the maximum peak detectors 62a, 62b, 62c. The peak number counter 63 counts the number of peaks corresponding to the detection of the particle R. The peak number counter 63 is a counter that counts the number of peaks of the signals $S_{31}, S_{32}, S_{33}$.

The particle type determination unit 64 receives the signals $S_{31}, S_{32}, S_{33}$ indicating the maximum peak points, which are output by the maximum peak detectors 62a, 62b, 62c. The particle type determination unit 64 determines the type of the particle R, on the basis of the signals $S_{31}, S_{32}, S_{33}$. The particle type determination unit 64 is a determination unit that determines the type of the particle R on the basis of the signals $S_{31}, S_{32}, S_{33}$.

For example, when detecting that the value of the signal $S_{32}$ is the same as the value of the signal $S_{33}$, the particle type determination unit 64 determines that the particle R is pollen. For example, when determining that the value of the signal $S_{32}$ is the same as the value of the signal $S_{33}$, the particle type determination unit 64 determines that the particle R is pollen. Moreover, when detecting that the value of the signal $S_{32}$ is different from the value of the signal $S_{33}$, the particle type determination unit 64 determines that the particle R is dust, for example. For example, when determining that the value of the signal $S_{32}$ is different from the value of the signal $S_{33}$, the particle type determination unit 64 determines that the particle R is dust. The signal $S_{32}$ indicates the maximum peak value of the output signal $S_{12}$ of the light reception element 161. The signal $S_{33}$ indicates the maximum peak value of the output signal $S_{13}$ of the light reception element 162.

For example, when detecting the signal $S_{31}$ and not detecting the signal $S_{32}$ and the signal $S_{33}$, the particle type determination unit 64 determines that the particle R is PM2.5 or PM10. The signal $S_{31}$ indicates the maximum peak value of the output signal $S_{11}$ of the light reception element 6. The light reception elements 161, 162 mainly receive the scattered light that enters directly. Hence, when the particle R is PM2.5 or the like, the values of the signal $S_{12}, S_{13}$ are small.

The particle type determination unit 64 is also employed in the micro object detection apparatuses 11, 12 that include the detection optical systems 50, 51. The micro object detection apparatuses 11, 12 determine the type of the particle R by the particle type determination unit 64, on the basis of the light intensity of the scattered light.

The micro object detection apparatus 11 according to the third embodiment includes the first detection optical system 52a and the second detection optical system 52b.

The first detection optical system 52a detects a particle whose light amount of the scattered light is comparatively small, by the light reception element 6. The particle whose light amount of the scattered light is comparatively small is PM2.5 or the like, for example.

On the other hand, the second detection optical system 52b detects a particle whose light amount of the scattered light is comparatively large, by the light reception elements 161, 162. The particle whose light amount of the scattered light is comparatively large is a particle having a larger particle size than PM2.5. The particle whose light amount of the scattered light is comparatively large is a particle such as pollen or dust, for example.

However, these are an example for describing the micro object detection apparatus 11. The type of the particle R of the detection target in the first detection optical system 52a and the second detection optical system 52b is not limited thereto.

If the fluorescence of the detection target particle R is detected, the first detection optical system 52a may be a detection optical system for detecting the fluorescence, for example. The light reception element 6 detects whether or not the detection target particle R has the fluorescence.

Moreover, the second detection optical system 52b can be a detection optical system that receives the scattered light from the particle R and detects the particle size or shape.

The irradiation light to the particle R acts as excitation light, to emit the fluorescence. The fluorescence has a wavelength $\lambda f$ that differs from the wavelength $\lambda e$ of the irradiation light. In general, the wavelength $\lambda f$ of the fluorescence is longer than the wavelength $\lambda e$ of the excitation light, in many cases. That is, it is the relationship of wavelength $\lambda f$>wavelength $\lambda e$.

In general, the fluorescence is weak. In addition, the first detection optical system 52a can collect a larger amount of scattered light. Hence, the first detection optical system 52a is suitable for detection of the fluorescence.

In order to determine whether or not the particle R is a fluorescent substance that emits the fluorescence, the fluorescence included in the scattered light from the particle R is divided and directed to the light reception element 6. The dividing method can be an optical filter provided in the prior stage of the light reception element 6, for example. The optical filter is a dichroic filter or the like, for example. The optical filter allows the light of the fluorescence wavelength $\lambda f$ to transmit. The optical filter blocks the light of the wavelength $\lambda e$ of the irradiation light. Whether or not the particle R is the fluorescent substance can be determined, in accordance with the light amount of the fluorescence, on the basis of the detection waveform output from the light reception element 6.

When the particle R is the fluorescent substance, the fluorescence is detected by the first detection optical system 52a. In addition, the scattered light is detected by the second detection optical system 52b. The scattered light detected by the second detection optical system 52b has the same wavelength as the wavelength $\lambda e$ of the irradiation light, for example. Thereby, the particle R can be determined to be the fluorescent substance.

On the other hand, when the particle R is not the fluorescent substance, the fluorescence is not detected by the first detection optical system 52a. The scattered light is detected by the second detection optical system 52b. The scattered light detected by the second detection optical system 52b has the same wavelength as the wavelength $\lambda e$ of the irradiation light, for example. Thereby, the particle R can be determined to not be the fluorescent substance.

As described above, the first detection optical system 52a and the second detection optical system 52b can select the detection method, according to the detection target particle R. The detection method is the light amount of the scattered light, the polarized light of the scattered light, the wavelength of the scattered light, or the like, for example.

As described above, in the detection optical system 52, the second detection optical system 52b is provided on the first converging mirror 103 side. Thereby, the reflection angle of the scattered light on the second converging mirror 104 can be made small. Thus, the decrease in the accuracy in detecting the polarized light components of the scattered light can be prevented.

Moreover, as described above, the opening AP is provided in the region on the first converging mirror 103 that the light beam 113c does not reach. The opening AP is positioned on the first converging mirror 103 that the scattered light reaches when the scattered light is reflected by the passage hole H. The opening AP includes a region surrounded by the points at which the scattered light reflected by the periphery of the passage hole H reaches the first converging mirror 103. Alternatively, the opening AP is positioned inside the region surrounded by the points at which the scattered light reflected by the periphery of the passage hole H reaches the first converging mirror 103. The opening AP is located at the position opposite to the passage hole H. The second detection optical system 52b that receives the scattered light that directly enters without being reflected by the second converging mirror 104 is provided at the position opposite to the passage hole H.

Thereby, the second detection optical system 52b can reduce the received light amount of the scattered light reflected by the second converging mirror 104. Thus, the decrease in the accuracy in detecting the polarized light components of the scattered light can be prevented.

The passage hole H and the opening AP are examples of the passage region. The passage region is a region that allows the light to pass therethrough. The passage region is a hole for example, and the passage region is a region or the like in which a transparent member is located for example.

The scattered light can reach the light reception element 6 by passing through the passage hole H, for example. The second converging mirror 104 includes the passage region (the passage hole H) that allows the scattered light directed to the light reception element 6 to pass therethrough. The scattered light can reach the second detection optical systems 52b, 53b by passing through the opening AP, for example. The first converging mirror 103 includes the passage region (the opening AP) that allows the scattered light directed to the second detection optical systems 52b, 53b to pass therethrough.

Moreover, the light reception element 6 can be located at the position of the passage hole H, for example. Moreover, the second detection optical systems 52b, 53b can be located at the position of the opening AP, for example.

As above, the detection optical systems 52, 53 of the micro object detection apparatus 11 according to the third embodiment can detect micro particulate matter such as PM2.5, pollen and the like, by one optical system.

Note that, when tams indicating positional relationships between components such as "parallel", "perpendicular", and "center" or terms indicating the shapes of components, are used in each of the above embodiments, these tams include a range considering manufacturing tolerance, variation in assembly, and the like. Hence, even when "substantially" is not recited in the claims, the range considering manufacturing tolerance, variation in assembly, and the like is included.

Although the embodiments of the present invention have been described as above, the present invention is not limited to these embodiments.

On the basis of the above embodiments, the detail of the invention will be recited as additional statement (1) to additional statement (4) in the following. In each of additional statement (1) to additional statement (4), reference numbers are given independently. Thus, for example, "additional statement 1" exists in both of additional statement (1) and additional statement (2).

Note that the feature of the device of additional statement (1) can be incorporated in the device of additional statement (2) to additional statement (4). Moreover, the feature of the device of additional statement (2) can be incorporated in the device of additional statement (3) or additional statement (4). Moreover, the feature of the device of additional statement (3) can be incorporated in the device of additional statement (4). Moreover, the device of additional statement (1), additional statement (2), or additional statement (3) can employ the method of additional statement (3). Moreover, the feature of the device of additional statement (1), the feature of the device of additional statement (2), the feature of the device of additional statement (3), and the feature of the device of additional statement (4) can be combined. In addition, the device obtained by combining those features can employ the method of additional statement (3).

<Additional Statement (1)>
<Additional Statement 1>

A micro object detection apparatus comprising:

a light radiation unit that radiates irradiation light on a particle in gas or liquid;

a first optical system that receives scattered light scattered by hitting the irradiation light against the particle, and detects an intensity of the scattered light; and a counter that counts the number of particles, on the basis of the intensity of the scattered light detected by the first optical system, wherein the first optical system includes a converging mirror and a light reception element, the converging mirror includes a first reflection region and a second reflection region, and directs the scattered light to the light reception element, the light reception element receives the scattered light and detects the intensity of the scattered light, the first reflection region has an elliptical mirror shape, and reflects the scattered light incident directly from the particle to direct the scattered light to the light reception element, by utilizing two focal point positions of an ellipse, the second reflection region reflects the scattered light incident directly from the particle to direct the scattered light to the first reflection region, so that the scattered light is reflected by the first region and is directed to the light reception element, and the second reflection region has an aspherical shape to give aberration to the scattered light reflected by the second reflection region, at a focal point position of the second reflection region.

<Additional Statement 2>

The micro object detection apparatus according to additional statement 1, wherein the aberration is larger than aberration generated by a spherical mirror that approximates the aspherical shape of the second reflection region.

<Additional Statement 3>

The micro object detection apparatus according to additional statement 1 or 2, wherein the aberration generated by the second reflection region is spherical aberration.

<Additional Statement 4>

The micro object detection apparatus according to additional statement 3, wherein the spherical aberration generated by the second reflection region is equal to or larger than 0.07 λrms.

<Additional Statement 5>

The micro object detection apparatus according to any one of additional statements 1 to 4, wherein the second reflection region includes a hole that allows the scattered light directed to the light reception element to pass therethrough, a second optical system that receives the scattered light incident directly without being reflected by the first reflection region is provided at a position opposite to the hole, and
the intensity of the scattered light is detected.

<Additional Statement 6>

The micro object detection apparatus according to additional statement 5, wherein the second optical system separates the scattered light accepted by the second optical system into polarized light components, and detects the intensity of the separated scattered light.

<Additional Statement 7>

The micro object detection apparatus according to additional statement 5 or 6, wherein the counter counts the number of particles, on the basis of the intensity of the scattered light detected by the second optical system.

<Additional Statement 8>

The micro object detection apparatus according to any one of additional statements 1 to 7, comprising a particle type determination unit that determines a type of the particle on the basis of the intensity of the scattered light detected by the first optical system or the second optical system.

<Additional Statement (2)>
<Additional Statement 1>

A micro object detection apparatus comprising:
a first optical system including a first reflection region, a second reflection region, and a light reception element,
wherein the first reflection region has an ellipsoidal shape, and reflects scattered light scattered when irradiation light hits a particle, to direct the scattered light to the light reception element, by utilizing two focal point positions of the ellipsoidal shape,
the second reflection region reflects scattered light coming from the particle to direct the scattered light to the first reflection region, so that the scattered light is directed to the light reception element by utilizing the ellipsoidal shape of the first reflection region, and
a light flux diameter of the scattered light reflected by the second reflection region is larger than the particle, at a position of the particle at which the scattered light is generated.

<Additional Statement 2>

The micro object detection apparatus according to additional statement 1, wherein the first reflection region is an elliptical mirror.

<Additional Statement 3>

The micro object detection apparatus according to additional statement 1 or 2, wherein the second reflection region generates a plurality of focal points that differ according to positions at which reflection of light occurs, to disperse the plurality of focal points.

<Additional Statement 4>

The micro object detection apparatus according to any one of additional statements 1 to 3, wherein
the second reflection region has an aspherical shape based on a spherical shape, and
the light flux diameter of the scattered light reflected by the second reflection region is larger than the light flux diameter of the scattered light of a case where the scattered light is reflected by a reflection region having the spherical shape as a basis for the aspherical shape, at the position of the particle at which the scattered light is generated.

<Additional Statement 5>

The micro object detection apparatus according to additional statement 4, wherein the second reflection region is an aspherical mirror.

<Additional Statement 6>

The micro object detection apparatus according to additional statement 4 or 5, wherein the second reflection region has the aspherical shape to give aberration to the scattered light reflected by the second reflection region, at the focal point position of the second reflection region.

<Additional Statement 7>

The micro object detection apparatus according to additional statement 6, wherein the aberration is larger than aberration generated by a spherical mirror that approximates the aspherical shape of the second reflection region.

<Additional Statement 8>

The micro object detection apparatus according to additional statement 6 or 7, wherein the aberration is spherical aberration.

<Additional Statement 9>

The micro object detection apparatus according to additional statement 8, wherein the spherical aberration is equal to or larger than 0.07 $\lambda$rms.

<Additional Statement 10>

The micro object detection apparatus according to additional statement 8, wherein the spherical aberration is equal to or larger than 6 $\lambda$pv.

<Additional Statement 11>

The micro object detection apparatus according to any one of additional statements 8 to 10, wherein the spherical aberration is equal to or smaller than 30 $\lambda$pv.

<Additional Statement 12>

The micro object detection apparatus according to any one of additional statements 8 to 10, wherein the spherical aberration is equal to or smaller than 50 $\lambda$pv.

<Additional Statement 13>

The micro object detection apparatus according to any one of additional statements 1 to 12, comprising: a light radiation unit that radiates the irradiation light on the particle.

<Additional Statement (3)>
<Additional Statement 1>

A micro object detection method for detecting a peak of an input signal corresponding to each particle in gas or liquid, to detect the number of particles, comprising:
determining that two local maximum values are quasi peaks corresponding to one particle, when a local minimum value exists between the two local maximum values of the input signal.

<Additional Statement 2>

The micro object detection method according to additional statement 1, comprising:
detecting a maximum peak of the input signal corresponding to the particle;
detecting a minimum peak of the input signal;
detecting positions of a first maximum peak, a second maximum peak, and the minimum peak, wherein the first maximum peak and the second maximum peak are two maximum peaks in the input signal; and
determining whether or not the maximum peaks are the quasi peaks corresponding to the one particle on the basis of the positions of the maximum peaks and the minimum peak.

<Additional Statement 3>

The micro object detection method according to additional statement 2, comprising: detecting whether or not the minimum peak exists between the first maximum peak and the second maximum peak.

<Additional Statement 4>

The micro object detection method according to additional statement 2, comprising: detecting whether or not the first maximum peak, the minimum peak, and the second maximum peak are detected in this order.

<Additional Statement 5>

The micro object detection method according to any one of additional statements 2 to 4, comprising: determining whether or not the first maximum peak and the second maximum peak are quasi peaks corresponding to one particle.

<Additional Statement 6>

The micro object detection method according to additional statement 5, comprising: determining whether or not the first maximum peak and the second maximum peak are the quasi peaks, on the basis of comparison between the first maximum peak and the minimum peak or comparison between the second maximum peak and the minimum peak.

<Additional Statement 7>

The micro object detection method according to additional statement 5, comprising: determining whether or not the first maximum peak and the second maximum peak are the quasi peaks, on the basis of comparison between a value calculated on the basis of the first maximum peak and the second maximum peak and the minimum peak.

<Additional Statement 8>

The micro object detection method according to additional statement 6 or 7, wherein the comparison is a difference between two values.

<Additional Statement 9>

The micro object detection method according to additional statement 6 or 7, wherein the comparison is a rate between two values.

<Additional Statement 10>

The micro object detection method according to any one of additional statements 1 to 9, comprising: determining that there is one particle, when determining that the local maximum values are the quasi peaks, and determining that there are two particles, when determining that the local maximum values are not the quasi peaks.

<Additional Statement 11>

The micro object detection method according to any one of additional statements 1 to 10, comprising: counting the number of particles.

<Additional Statement 12>

The micro object detection method according to any one of additional statements 1 to 11, comprising: calculating a number concentration or a weight concentration of the particles, on the basis of the number of particles.

<Additional Statement 13>

A micro object detection apparatus for detecting a peak of an input signal corresponding to each particle in gas or liquid, to detect the number of particles, wherein the micro object detection apparatus determines that two local maximum values are quasi peaks corresponding to one particle, when a local minimum value exists between the two local maximum values of the input signal.

<Additional Statement 14>

The micro object detection apparatus according to additional statement 13, comprising:

a maximum peak detector that detects a maximum peak of the input signal corresponding to the particle;

a minimum peak detector that detects a minimum peak of the input signal; and an adjacent peak detector that detects positions of a first maximum peak, a second maximum peak, and the minimum peak, wherein the first maximum peak and the second maximum peak are two maximum peaks in the input signal, wherein the micro object detection apparatus determines whether or not the maximum peaks are quasi peaks corresponds to one particle on the basis of the positions of the maximum peaks and the minimum peak.

<Additional Statement 15>

The micro object detection apparatus according to additional statement 14, comprising: an adjacent peak detector that detects whether or not the minimum peak exists between the first maximum peak and the second maximum peak, in the order of detection in the maximum peak detector and the minimum peak detector.

<Additional Statement 16>

The micro object detection apparatus according to additional statement 14, comprising: an adjacent peak detector that detects whether or not the maximum peak detector and the minimum peak detector detect the first maximum peak, the minimum peak, and the second maximum peak in this order.

<Additional Statement 17>

The micro object detection apparatus according to any one of additional statements 14 to 16, comprising: a peak difference determination unit that determines whether or not the first maximum peak and the second maximum peak detected by the maximum peak detector are quasi peaks corresponds to one particle.

<Additional Statement 18>

The micro object detection apparatus according to additional statement 17, wherein the peak difference determination unit determines whether or not the first maximum peak and the second maximum peak are the quasi peaks, on the basis of comparison between the first maximum peak and the minimum peak or comparison between the second maximum peak and the minimum peak.

<Additional Statement 19>

The micro object detection apparatus according to additional statement 17, wherein the peak difference determination unit determines whether or not the first maximum peak and the second maximum peak are the quasi peaks, on the basis of comparison between a value calculated on the basis of the first maximum peak and the second maximum peak and the minimum peak.

<Additional Statement 20>

The micro object detection apparatus according to additional statement 18 or 19, wherein the comparison is a difference between two values.

<Additional Statement 21>

The micro object detection apparatus according to additional statement 18 or 19, wherein the comparison is a rate between two values.

<Additional Statement 22>

The micro object detection apparatus according to any one of additional statements 13 to 21, comprising: a quasi peak elimination unit that outputs a result indicating that there is one particle, when it is determined that the maximum peaks are the quasi peaks, and outputs a result indicating that there are two particles, when the peak difference determination unit determines that the maximum peaks are not the quasi peaks.

<Additional Statement 23>

The micro object detection apparatus according to any one of additional statements 13 to 22, comprising: a counter that counts the number of particles.

<Additional Statement 24>

The micro object detection apparatus according to any one of additional statements 13 to 23, wherein the micro object detection apparatus calculates a number concentration or a weight concentration of the particles, on the basis of the number of particles.

<Additional Statement (4)>
<Additional Statement 1>

A micro object detection apparatus comprising:

a first optical system that includes a first reflection region, a second reflection region, and a first light reception element, and directs scattered light scattered when irradiation light hits a particle, to the first light reception element, by reflecting the scattered light by the first reflection region and the second reflection region; and a second optical system that receives the scattered light, wherein the scattered light is directed to the first light reception element by providing a first passage region in the second reflection region, and the scattered light is directed to the second optical system by providing a second passage region in the first reflection region.

<Additional Statement 2>

The micro object detection apparatus according to additional statement 1, wherein the second passage region includes a region surrounded by a periphery shape of the first passage region projected on the first reflection region by the scattered light.

<Additional Statement 3>

The micro object detection apparatus according to additional statement 1 or 2, wherein the second passage region is located at a position opposite to the first passage region.

<Additional Statement 4>

The micro object detection apparatus according to any one of additional statements 1 to 3, wherein the first passage region is a hole provided in the second reflection region.

<Additional Statement 5>

The micro object detection apparatus according to any one of additional statements 1 to 4, wherein the second passage region is a hole provided in the first reflection region.

<Additional Statement 6>

The micro object detection apparatus according to any one of additional statements 1 to 7, wherein the second passage region is positioned inside a region surrounded by a periphery shape of the first passage region projected on the first reflection region by the scattered light.

<Additional Statement 7>

The micro object detection apparatus according to any one of additional statements 1 to 6, wherein the micro object detection apparatus determines a type of the particle, on the basis of an intensity of the scattered light detected by the first light reception element.

<Additional Statement 8>

The micro object detection apparatus according to any one of additional statements 1 to 7, wherein the micro object detection apparatus determines whether or not the particle is a particulate matter, on the basis of an intensity of the scattered light detected by the first light reception element.

<Additional Statement 9>

The micro object detection apparatus according to any one of additional statements 1 to 8, wherein the micro object detection apparatus determines whether or not the particle is a micro particulate matter, on the basis of an intensity of the scattered light detected by the first light reception element.

<Additional Statement 10>

The micro object detection apparatus according to any one of additional statements 1 to 9, comprising: a particle type determination unit that determines a type of the particle.

<Additional Statement 11>

The micro object detection apparatus according to any one of additional statements 1 to 10, wherein the first reflection region has an ellipsoidal shape, and reflects the scattered light coming from the particle to direct the scattered light to the first light reception element, by utilizing two focal point positions of the ellipsoidal shape.

<Additional Statement 12>

The micro object detection apparatus according to additional statement 11, wherein the particle is positioned in a region of a first focal point of the first reflection region.

<Additional Statement 13>

The micro object detection apparatus according to additional statement 11 or 12, wherein the first light reception element is positioned in a region of a second focal point of the first reflection region.

<Additional Statement 14>

The micro object detection apparatus according to any one of additional statements 1 to 13, wherein the second reflection region reflects the scattered light coming from the particle to direct the scattered light to the first reflection region, and the scattered light is reflected by the first reflection region and is directed to the first light reception element.

<Additional Statement 15>

The micro object detection apparatus according to any one of additional statements 1 to 14, wherein the second reflection region has a spherical shape.

<Additional Statement 16>

The micro object detection apparatus according to any one of additional statements 1 to 15, wherein the second reflection region is a spherical mirror.

<Additional Statement 17>

The micro object detection apparatus according to additional statement 15 or 16, wherein a third focal point of the second reflection region is positioned at a position of the first focal point.

<Additional Statement 18>

The micro object detection apparatus according to any one of additional statements 1 to 14, wherein the second reflection region has an aspherical shape based on a spherical shape.

<Additional Statement 19>

The micro object detection apparatus according to any one of additional statements 1 to 14 and 18, wherein the second reflection region is an aspherical mirror based on a spherical shape.

<Additional Statement 20>

The micro object detection apparatus according to additional statement 18 or 19, wherein a third focal point of the second reflection region is positioned at a position of the first focal point.

<Additional Statement 21>

The micro object detection apparatus according to any one of additional statements 18 to 20, wherein a light flux diameter of the scattered light reflected by the second reflection region is larger than a light flux diameter of the scattered light of a case where the scattered light is reflected by the reflection region having the spherical shape as a basis for the aspherical shape, at a position of the particle at which the scattered light is generated.

<Additional Statement 22>

The micro object detection apparatus according to any one of additional statements 1 to 14 and 18 to 21, wherein the second reflection region generates a plurality of focal points to disperse the focal points.

<Additional Statement 23>

The micro object detection apparatus according to any one of additional statements 1 to 14 and 18 to 22, wherein the second reflection region generates spherical aberration.

<Additional Statement 24>

The micro object detection apparatus according to additional statement 23, wherein the spherical aberration generated by the second reflection region is equal to or larger than 0.07 λrms.

<Additional Statement 25>

The micro object detection apparatus according to additional statement 23, wherein the spherical aberration generated by the second reflection region is equal to or larger than 6 λpv.

<Additional Statement 26>

The micro object detection apparatus according to any one of additional statements 23 to 25, wherein the spherical aberration generated by the second reflection region is equal to or smaller than 30 λpv.

<Additional Statement 27>

The micro object detection apparatus according to any one of additional statements 23 to 25, wherein the spherical aberration generated by the second reflection region is equal to or smaller than 50 λpv.

<Additional Statement 28>

The micro object detection apparatus according to any one of additional statements 1 to 27, wherein the first optical system detects light having a different wavelength from a wavelength of the irradiation light, among the scattered light.

<Additional Statement 29>

The micro object detection apparatus according to any one of additional statements 1 to 28, wherein the first optical system detects fluorescence included in the scattered light.

<Additional Statement 30>

The micro object detection apparatus according to any one of additional statements 1 to 29, wherein the second optical system separates the scattered light directed to the second optical system into different polarized light components, and detects intensities of the separated scattered light.

<Additional Statement 31>

The micro object detection apparatus according to additional statement 30, wherein the second optical system includes a polarized light separating element that separates the scattered light into the polarized light components.

<Additional Statement 32>

The micro object detection apparatus according to additional statement 31, wherein the polarized light separating element is a polarization prism.

<Additional Statement 33>

The micro object detection apparatus according to any one of additional statements 30 to 32, wherein the second optical system includes a second light reception element and a third light reception element that receive the scattered light separated into the polarized light components.

<Additional Statement 34>

The micro object detection apparatus according to additional statement 33, wherein the second light reception element receives the scattered light of a first polarized light component, and the third light reception element receives the scattered light of a second polarized light component that is orthogonal to the scattered light of the first polarized light component.

<Additional Statement 35>

The micro object detection apparatus according to additional statement 33 or 34, wherein the second optical system includes a first light converging element that converges the scattered light toward the second light reception element and the third light reception element.

<Additional Statement 36>

The micro object detection apparatus according to additional statement 35, wherein the first light converging element is a first converging lens.

<Additional Statement 37>

The micro object detection apparatus according to any one of additional statements 30 to 36, wherein the micro object detection apparatus determines a type of the particle, on the basis of the intensities of the scattered light detected by the second optical system.

<Additional Statement 38>

The micro object detection apparatus according to any one of additional statements 30 to 37, wherein the micro object detection apparatus determines whether the particle is a spherical shape or other than a spherical shape, on the basis of the intensities of the scattered light separated into the polarized light components.

<Additional Statement 39>

The micro object detection apparatus according to any one of additional statements 30 to 38, wherein the micro object detection apparatus determines that a shape of the particle is a spherical shape, when detecting that the intensities of the scattered light separated into the polarized light components are the same value.

<Additional Statement 40>

The micro object detection apparatus according to any one of additional statements 30 to 39, wherein the micro object detection apparatus determines that a shape of the particle is other than a spherical shape when detecting that the intensities of the scattered light separated into the polarized light components are different values.

<Additional Statement 41>

The micro object detection apparatus according to any one of additional statements 30 to 40, wherein the particle type determination unit determines that the particle is pollen, when detecting that the intensities of the scattered light separated by the second optical system are the same value.

<Additional Statement 42>

The micro object detection apparatus according to any one of additional statements 30 to 41, wherein the particle type determination unit determines that the particle is dust, when detecting that the intensities of the scattered light separated by the second optical system are different values.

<Additional Statement 43>

The micro object detection apparatus according to any one of additional statements 30 to 42, comprising: a particle type determination unit that determines a type of the particle.

<Additional Statement 44>

The micro object detection apparatus according to any one of additional statements 1 to 43, wherein the micro object detection apparatus detects a maximum peak of an intensity of the scattered light output from the first optical system.

<Additional Statement 45>

The micro object detection apparatus according to any one of additional statements 1 to 44, wherein the micro object detection apparatus detects a maximum peak of an intensity of the scattered light output from the second optical system.

<Additional Statement 46>

The micro object detection apparatus according to any one of additional statements 1 to 45, comprising: a maximum peak detector that detects a maximum peak of an intensity of the scattered light.

<Additional Statement 47>

The micro object detection apparatus according to additional statement 44, wherein the micro object detection apparatus detects a minimum peak of the intensity of the scattered light output from the first optical system.

<Additional Statement 48>

The micro object detection apparatus according to additional statement 45, wherein the micro object detection apparatus detects a minimum peak of the intensity of the scattered light output from the second optical system.

<Additional Statement 49>

The micro object detection apparatus according to any one of additional statements 1 to 48, comprising: a minimum peak detector that detects a minimum peak of an intensity of the scattered light.

<Additional Statement 50>

The micro object detection apparatus according to additional statement 47, wherein two maximum peaks detected from the first optical system are a first maximum peak and a second maximum peak, and the micro object detection apparatus determines whether or not the first maximum peak and the second maximum peak are quasi peaks corresponding to one particle.

<Additional Statement 51>

The micro object detection apparatus according to additional statement 48, wherein two maximum peaks detected from the second optical system are a first maximum peak and a second maximum peak, and the micro object detection apparatus determines whether or not the first maximum peak and the second maximum peak are quasi peaks corresponding to one particle.

<Additional Statement 52>

The micro object detection apparatus according to additional statement 50 or 51, comprising: a peak difference determination unit that determines whether or not the quasi peaks exist.

<Additional Statement 53>

The micro object detection apparatus according to any one of additional statements 1 to 49, comprising: a peak difference determination unit that determines whether or not a quasi peak exists.

<Additional Statement 54>

The micro object detection apparatus according to any one of additional statements 50 to 52, wherein the micro object detection apparatus determines whether or not the first maximum peak and the second maximum peak are the quasi peaks, on the basis of comparison between the first maximum peak and the minimum peak or comparison between the second maximum peak and the minimum peak.

<Additional Statement 55>

The micro object detection apparatus according to any one of additional statements 50 to 52, wherein the micro object detection apparatus determines whether or not the first maximum peak and the second maximum peak are the quasi peaks, on the basis of comparison between a value calculated on the basis of the first maximum peak and the second maximum peak and the minimum peak.

<Additional Statement 56>

The micro object detection apparatus according to additional statement 54 or 55, wherein the comparison is a difference between two values.

<Additional Statement 57>

The micro object detection apparatus according to additional statement 54 or 55, wherein the comparison is a rate between two values.

<Additional Statement 58>

The micro object detection apparatus according to any one of additional statements 50 to 52 and additional statements 54 to 57, wherein the micro object detection apparatus determines whether or not the quasi peaks exist, on the basis of an order of detection of the maximum peaks and the minimum peak.

<Additional Statement 59>

The micro object detection apparatus according to any one of additional statements 50 to 52 and additional statements 54 to 58, wherein the micro object detection apparatus determines that the quasi peaks exist, when the first maximum peak, the minimum peak, and the second maximum peak are detected in this order.

<Additional Statement 60>

The micro object detection apparatus according to any one of additional statements 50 to 52 and additional statements 54 to 59, comprising: an adjacent peak determination unit that determines whether or not the minimum peak exists between the first maximum peak and the second maximum peak.

<Additional Statement 61>

The micro object detection apparatus according to any one of additional statements 1 to 49 and additional statement 53, comprising: an adjacent peak determination unit that determines whether or not a minimum peak exists between a first maximum peak and a second maximum peak.

<Additional Statement 62>

The micro object detection apparatus according to any one of additional statements 58 to 60, wherein the micro object detection apparatus determines that there is one particle, when determining that the quasi peaks exist, and that there are two particles, when determining that the quasi peaks do not exist.

<Additional Statement 63>

The micro object detection apparatus according to any one of additional statements 58 to 60, comprising: a quasi peak elimination unit that outputs a result indicating that there is one particle, when determining that the quasi peaks exist, and outputs a result indicating that there are two particles, when determining that the quasi peaks do not exist.

<Additional Statement 64>

The micro object detection apparatus according to any one of additional statements 1 to 57, comprising: a quasi peak elimination unit that outputs a result indicating that there is one particle, when determining that quasi peaks exist, and outputs a result indicating that there are two particles, when determining that the quasi peaks do not exist.

<Additional Statement 65>

The micro object detection apparatus according to additional statement 62, wherein the micro object detection apparatus counts the number of particles, on the basis of a determination result of the quasi peaks.

<Additional Statement 66>

The micro object detection apparatus according to additional statement 63 or 64, wherein the micro object detection apparatus counts the number of particles output by the quasi peak elimination unit.

<Additional Statement 67>

The micro object detection apparatus according to any one of additional statements 1 to 66, wherein the micro object detection apparatus counts the number of particles, on the basis of an intensity of the scattered light detected by the first optical system and the second optical system.

<Additional Statement 68>

The micro object detection apparatus according to any one of additional statements 1 to 67, comprising: a counter that counts the number of particles.

<Additional Statement 69>

The micro object detection apparatus according to any one of additional statements 1 to 68, wherein the micro object detection apparatus calculates a number concentration or a weight concentration of the particles, on the basis of the calculated number of particles.

<Additional Statement 70>

The micro object detection apparatus according to any one of additional statements 1 to 69, comprising: a light radiation unit that radiates the irradiation light on the particle.

<Additional Statement 71>

The micro object detection apparatus according to additional statement 70, wherein the light radiation unit includes a light source that radiates the irradiation light.

<Additional Statement 72>

The micro object detection apparatus according to additional statement 70 or 71, wherein the light radiation unit includes a second light converging element that converges the irradiation light.

<Additional Statement 73>

The micro object detection apparatus according to additional statement 72, wherein the second light converging element is a second converging lens.

<Additional Statement 74>

The micro object detection apparatus according to additional statement 72 or 73, wherein the light radiation unit includes a holding unit that holds at least one of the light source and the second light converging element.

<Additional Statement 75>

The micro object detection apparatus according to additional statement 74, wherein the holding unit is connected to the first optical system.

DESCRIPTION OF REFERENCE CHARACTERS

11, 12, 13 micro object detection apparatus, 500, 520 optical system of micro object detection apparatus, 50, 51, 52, 53 detection optical system, 52a, 53a first detection optical system, 52b, 53b second detection optical system, 10 laser light radiation unit, 20 scattered light receiving unit, 1 laser light emitting element, 2 lens, 3 irradiation light, 4 beam trap, 5a suction port, 5b discharge port, 6 light reception element, 60, 65, 70 detection circuit unit, 61, 61a, 61b, 61c amplifier circuit, 62, 62a, 62b, 62c, 71 maximum peak detector, 63 peak number counter, 64 particle type determination unit, 72 minimum peak detector, 73 adjacent peak determination unit, 74 peak difference determination unit, 75 quasi peak elimination unit, 76 peak detector, 80 particle determination unit, 91 radiation unit holder, 101, 103 first converging mirror, 102, 104 second converging mirror, 101a, 102a, 103a, 104a reflection surface, 111a, 111b light beam on first path, 112 light beam on second path, 113a, 113b, 113c, 113d, 113e light beam on third path, 114, 114p, 114s light beam on fourth path, 160 lens, 161, 162 light reception element, 163 polarization prism, 163p, 163s projection surface, 164 reflection surface, 165 lens portion, 200 scattered light, 300 parallel flat plate, A output value of signal $S_1$, Ap, $Ap_1$, $Ap_2$, $Ap_3$, $Ap_4$, $Ap_5$, $Ap_6$ peak point, AP opening, D detection region, DL hole, ds distance, Ip, Is light intensity, P passage region, $P_1$, $P_2$, $P_3$, $P_4$, $P_5$, $P_6$ peak value, $\Delta P_1$, $\Delta P_2$, $\Delta P_0$ value, $F_1$, $F_2$, $F_3$ waveform, $G_1$, $G_2$ position, R particle, D detection region, P passage region, L scattered light, Ls lateral scattered light, Lfs forward scattered light, Lbs backward scattered light, $r_1$, $r_2$, $r_3$ radius, $S_1$, $S_{11}$, $S_{12}$, $S_{13}$, $S_2$, $S_{21}$, $S_{22}$, $S_{23}$, $S_3$, $S_{31}$, $S_{32}$, $S_{33}$, $S_4$, $S_5$, $S_6$, $S_7$ signal, tc center of waveform, O center axis of design of second converging mirror 102, H passage hole $U_1$, $U_2$, $U_3$ focal point position, $\lambda e$, $\lambda f$ wavelength.

What is claimed is:

1. A micro object detection apparatus comprising:
   a first optical system including a first reflection region, a second reflection region, and a light reception element,
   wherein the first reflection region has an ellipsoidal shape, and reflects scattered light scattered when irradiation light hits a particle, to direct the scattered light to the light reception element, by utilizing two focal point positions of the ellipsoidal shape,
   the second reflection region reflects scattered light coming from the particle to direct the scattered light to the first reflection region, so that the scattered light is directed to the light reception element by utilizing the ellipsoidal shape of the first reflection region, and
   a light flux diameter of the scattered light reflected by the second reflection region is larger than the particle, at a position of the particle at which the scattered light is generated.

2. The micro object detection apparatus according to claim 1, wherein the second reflection region generates a plurality of focal points that differ according to positions at which reflection of light occurs, to disperse the plurality of focal points.

3. The micro object detection apparatus according to claim 1, wherein
   the second reflection region has an aspherical shape based on a spherical shape, and
   a light flux diameter of the scattered light reflected by the second reflection region is larger than a light flux diameter of the scattered light of a case where the scattered light is reflected by a reflection region having the spherical shape as a basis for the aspherical shape, at the position of the particle at which the scattered light is generated.

4. The micro object detection apparatus according to claim 2, wherein
   the second reflection region has an aspherical shape based on a spherical shape, and
   a light flux diameter of the scattered light reflected by the second reflection region is larger than a light flux diameter of the scattered light of a case where the scattered light is reflected by a reflection region having the spherical shape as a basis for the aspherical shape, at the position of the particle at which the scattered light is generated.

* * * * *